(12) United States Patent
Call et al.

(10) Patent No.: US 6,938,777 B2
(45) Date of Patent: Sep. 6, 2005

(54) METHOD FOR REMOVING SURFACE DEPOSITS OF CONCENTRATED COLLECTED PARTICLES

(75) Inventors: Charles J. Call, Albuquerque, NM (US); Patrick T. Call, West Richland, WA (US); Vanessa M. Kenning, Kennewick, WA (US); Eric Hanczyc, Renton, WA (US); Andrew Kamholz, Albuquerque, NM (US)

(73) Assignee: MesoSystems Technology, Inc., Albuquerque, NM (US)

( * ) Notice: Subject to any disclaimer, the term of this patent is extended or adjusted under 35 U.S.C. 154(b) by 114 days.

(21) Appl. No.: 10/366,595

(22) Filed: Feb. 11, 2003

(65) Prior Publication Data

US 2004/0016680 A1 Jan. 29, 2004

Related U.S. Application Data

(63) Continuation-in-part of application No. 09/955,481, filed on Sep. 17, 2001, now Pat. No. 6,695,146.
(60) Provisional application No. 60/355,915, filed on Feb. 11, 2002.

(51) Int. Cl.[7] .............................. B07B 7/00; B07B 13/00
(52) U.S. Cl. ........................... 209/143; 209/49; 209/58; 209/59; 73/863.22
(58) Field of Search .................................. 209/136, 137, 209/138, 142, 143, 49, 58, 59, 55, 644, 657, 932; 95/31, 32, 33; 55/462; 73/28.04, 28.05, 863.22

(56) References Cited

U.S. PATENT DOCUMENTS

| | | | |
|---|---|---|---|
| 3,001,914 A | 9/1961 | Andersen | |
| 3,518,815 A * | 7/1970 | McFarland et al. | 73/863.22 |
| 3,760,630 A * | 9/1973 | Brumbaugh | 73/28.05 |
| 3,901,798 A | 8/1975 | Peterson | |
| 3,922,905 A | 12/1975 | Roth | |
| 3,972,226 A | 8/1976 | Rountree et al. | |
| 4,473,384 A * | 9/1984 | Lefkowitz | 55/290 |
| 4,670,135 A | 6/1987 | Marple et al. | |
| 4,767,524 A | 8/1988 | Yeh et al. | |
| 4,961,966 A | 10/1990 | Stevens et al. | |
| 5,040,424 A * | 8/1991 | Marple et al. | 73/863.23 |
| 5,304,125 A | 4/1994 | Leith | |
| 5,425,802 A | 6/1995 | Burton et al. | |
| 5,533,406 A | 7/1996 | Geise | |
| 5,776,754 A | 7/1998 | Caldwell | |
| 5,786,894 A | 7/1998 | Shields et al. | |
| 5,932,795 A * | 8/1999 | Koutrakis et al. | 73/28.01 |
| 6,101,886 A | 8/2000 | Brenizer et al. | |
| 6,110,247 A | 8/2000 | Birmingham et al. | |
| 6,217,636 B1 | 4/2001 | McFarland | |
| 6,240,768 B1 | 6/2001 | Lemonnier | |
| 6,276,016 B1 * | 8/2001 | Springer | 14/71.1 |
| 6,284,025 B1 | 9/2001 | Kreisberg et al. | |
| 6,363,800 B1 * | 4/2002 | Call et al. | 73/863.22 |
| 6,435,043 B1 | 8/2002 | Ferguson et al. | |
| 6,695,146 B2 * | 2/2004 | Call et al. | 209/143 |

FOREIGN PATENT DOCUMENTS

JP          59196713 A  * 11/1984  ........... B01D/46/00

* cited by examiner

Primary Examiner—Donald P. Walsh
Assistant Examiner—Joseph Rodriguez
(74) Attorney, Agent, or Firm—Ronald M. Anderson

(57) ABSTRACT

A method and apparatus for removing concentrated spots of collected particulates from an impact collection surface, and transferring those particulates into a container suitable for preparing a liquid sample. A jet of fluid can be utilized to remove and transfer the particulates. If a liquid jet is employed, care is taken to minimize the quantity of liquid to avoid unnecessarily diluting the sample. A mechanical scraper can alternatively be employed to remove and transfer the particulates into the container. The scraper can be rinsed with liquid or vibrated to remove the particulates. Alternatively, the portion of the surface containing a specific spot of particulates can be removed and placed into a container.

5 Claims, 21 Drawing Sheets

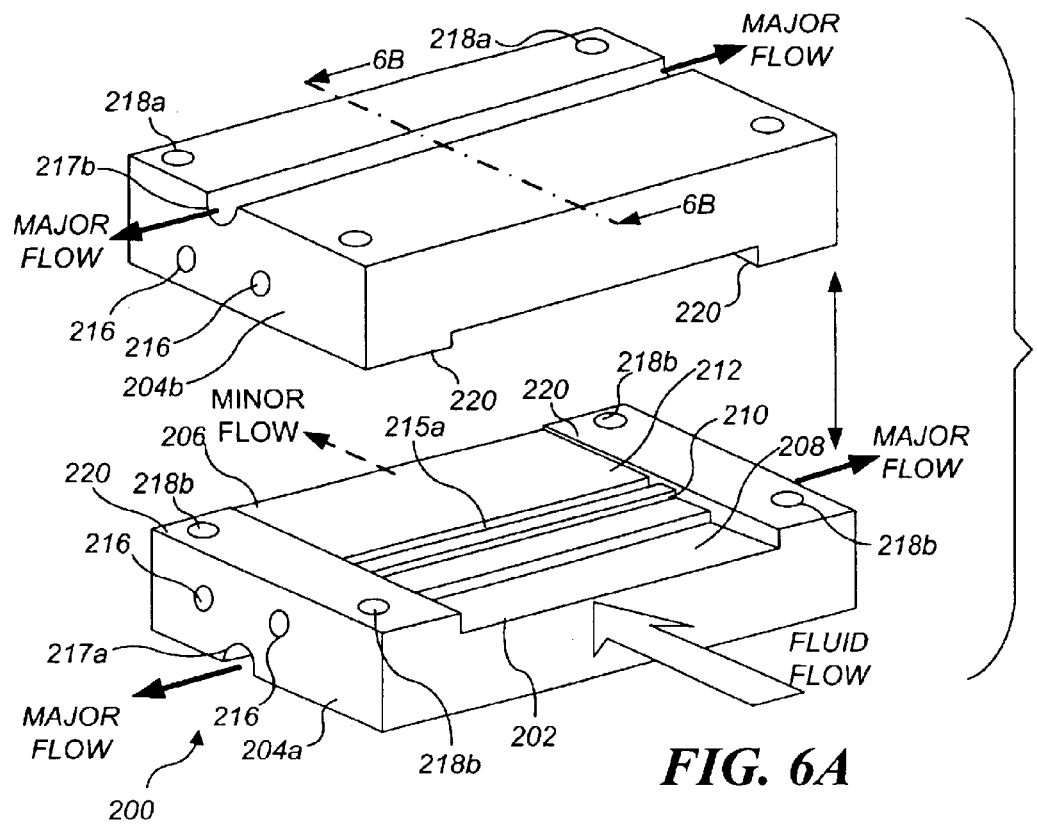
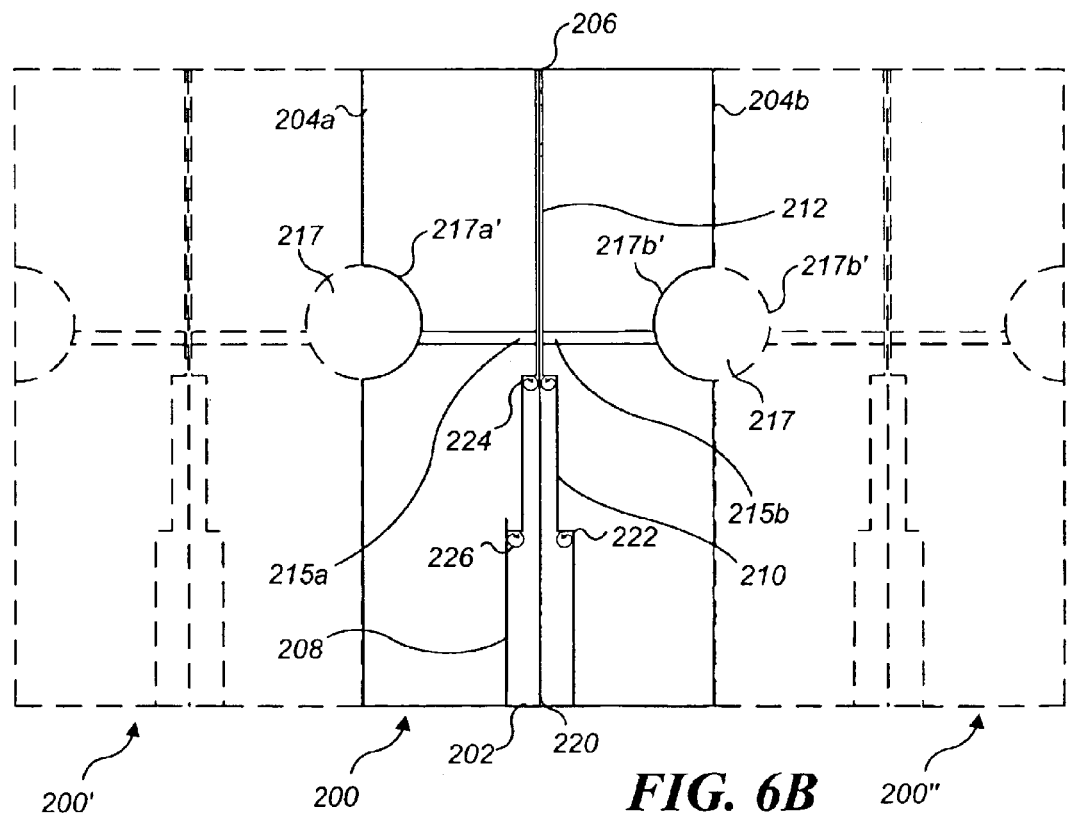
FIG. 6A
FIG. 6B

METHOD FOR REMOVING SURFACE DEPOSITS OF CONCENTRATED COLLECTED PARTICLES

RELATED APPLICATIONS

This application is based on a prior copending provisional application Ser. No. 60/355,915, filed on Feb. 11, 2002, and is further a continuation in part of a prior copending application Ser. No. 09/955,481, filed on Sep. 17, 2001, and issued as U.S. Pat. No. 6,695,146 B2 on Feb. 24, 2004, the benefits of the filing dates of which are hereby claimed under 35 U.S.C. §119(e) and 35 U.S.C. §120.

FIELD OF THE INVENTION

This invention generally relates to methods for removing collected particulates from a collection surface, and more specifically, to methods for transferring collected particulates from an impact collection surface to a more suitable sample container.

BACKGROUND OF THE INVENTION

The separation and collection of particulates/aerosols from an airstream (or other fluid streams) is of concern in several contexts. In some cases, the goal may be to simply remove the particulates/aerosols from the fluid stream, thereby cleaning or purifying the fluid. Often it is desired to remove all particulates, regardless of composition, if the particulates are above a certain size. For example, automobile painting and the fabrication of silicon chips in clean rooms represent two situations in which all particulates large enough to result in an inferior product are desirably removed from the processing environment.

In other cases, particulates are collected for analysis to determine the type and concentration of such particulates/aerosols entrained in the fluid. For example, this technology may be employed in the detection of airborne biological or chemical warfare agents, the detection of biological contamination in confined spaces, such as aircraft or hospitals, or the detection of industrial pollutants (either in ambient fluid or in the effluent of smokestacks).

Much effort has been expended in the past in the detection and classification of particulates or aerosols in fluid streams. Impactors have been used for collecting aerosol particulates for many decades. In the earliest embodiments, a stream of fluid containing the particulates was accelerated toward an impactor plate. Due to their inertia, the particulates striking the impactor plate were collected on its surface, while the fluid was deflected to the side. With these types of impactors, only larger particulates could be collected, since particulates below a certain "cut size" were carried away by the fluid stream.

However, a significant disadvantage of such an impactor is the deposition of particulates on surfaces of the impactor other than the intended collection surfaces. This phenomenon reduces the accuracy of measurement of total particulate mass concentration and of the size-fractionation of particulates, since such losses cannot be accurately estimated for aerosols or particulates of varying size, shape, or chemistry. Additionally, particulates may either become re-entrained in the fluid stream, or may bounce off the impactor's collection surface upon impact. To remedy this problem, "virtual" impactors have been developed that separate particulates from a fluid stream with techniques other than direct impaction. Virtual impactors may operate on a number of different principles, but all avoid actual "impact" as a means to separate particulates from a fluid in which the particulates are entrained and rely on differences in particulate mass to induce inertial separation. Specifically, a particulate-laden fluid stream is directed toward a surface presenting an obstruction to the forward movement of the fluid stream. The surface includes a void at the point where the particulates would normally impact the surface. When a major portion of the fluid stream changes direction to avoid the obstruction presented by the surface, fine particulates remain entrained in the deflected major portion of the fluid stream. Heavier or denser particulates, on the other hand, fail to change direction and are collected in a region of relatively stagnant fluid (a "dead zone") that is created near the surface. The heavier particulates entrained in a minor portion of the fluid stream enter the void defined through the surface, where they can be captured or analyzed.

Some examples of virtual impactors can be found in U.S. Pat. Nos. 3,901,798; 4,670,135; 4,767,524; 5,425,802; and 5,533,406. Because typical virtual impactors do not actually collect particulates themselves, but merely redirect them into two different fluid streams according to their mass, they are essentially free of the problems of particulate bounce and particulate re-entrainment associated with actual impactor devices. Still, particulate "wall loss," i.e., unintended deposition of particulates on various surfaces of virtual impactor structures, especially at curved or bent portions, remains a challenge with some designs of virtual impactors, because typically, many stages or layers of virtual impactors are required to complete particulate separation.

An additional aspect of the collection of fluid-entrained particulates, especially with respect to particulates that will be analyzed to determine a type and concentration of particulates, relates to when the collected particulates are to be analyzed. A common practice is to sample a fluid for a period of time, and then analyze the collected sample immediately, or at least as soon as practical. Depending on the nature of the particulates for which the fluid is being sampled, immediate analysis may be required. For example, if chemical or biological agents that pose an immediate health threat are suspected, real time analysis is preferred to enable protective measures to be taken immediately, before irreversible harm can occur. However, there are also many applications, such as routine monitoring of smokestacks and wastewater discharge, in which only a portion of the collected sample might need to be analyzed shortly after collection, while other portions are best archived for later analysis.

Archival samples can be prepared by taking a collected sample and manually splitting that sample into various fractions, including a first fraction to be analyzed relatively soon, and one or more additional portions to be archived for possible later analysis. While archival samples prepared by such a method are useful, the manual nature of such a method is time consuming and costly. Furthermore, during each step in which a sample is handled or manipulated (collection, separation, storage, and analysis), there is a significant chance that the sample will be inadvertently contaminated. It would thus be desirable to provide a method and apparatus that more readily enables archival samples to be prepared, with a minimal risk of contamination.

It should also be noted that the manner in which samples are collected affects the usefulness of the samples for archival purposes. Archival samples are often employed to determine more information about an event occurring at a specific time. For example, archival data collected from a smokestack might be used to determine at what time higher emissions occurred. That time could then be applied to analyze the process and equipment utilizing the smokestack to isolate the factors causing the excess emissions, so that the problem can be corrected. If the archival sample is merely a single sample collected over a 24-hour period, rather than 24 samples collected each hour for 24 hours, then little information can be obtained about when the excess emissions actually occurred, making it more difficult to determine the cause of the excess emissions. It would be therefore be desirable to provide a method and apparatus capable of providing archival samples for successive relatively short sampling periods, and which include time indexing enabling a specific archival sample to be correlated with a specific time at which the sample was taken.

Accordingly, a need exists to develop a method and apparatus capable of providing time-indexed archival samples with minimal operator effort, and minimal chance of contamination. Such archival samples desirably should include a high concentration of particulates, so that the archival samples are compact and require minimal storage space. Preferably, a virtual impactor that efficiently separates particulates from a fluid stream might be employed to collect the particulates.

Yet another aspect of the collection of fluid-entrained particulates, especially with respect to particulates collected with an impact collector, relates to how the collected particulates are to be analyzed. Most analytical techniques require a liquid sample. Regardless of how effective impact collectors are at removing particulates from a fluid stream (such as air), the collected particulates generally cannot readily be analyzed while remaining deposited on the impact collection surface. It would be desirable to provide a method and apparatus for removing collected particulates from an impact collection surface, and to transfer such particulates to a container that can be utilized to prepare a liquid sample. It would be further be desirable to provide an integrated system capable of collecting particulates from a fluid stream using an impact collector, and then transferring the collected particulates from the impact collector to a container suitable for preparing a liquid sample.

It should be noted that when a liquid sample is prepared using collected particulates, the amount of liquid used to prepare the liquid sample plays a significant factor in determining the concentration of the liquid sample. Higher concentration samples are generally require less challenging analytical techniques to analyze and are thus preferred. Therefore, it would be desirable for the method and apparatus employed to transfer collected particulates from an impact collection surface to a suitable container utilizing little or no liquid to unduly dilute the sample.

SUMMARY OF THE INVENTION

The present invention is directed to a method and apparatus for concentrating, collecting, and depositing "spots" of particulates from a fluid onto a solid collection surface, and then transferring the collected particulates to a container than can be utilized to store a liquid sample. Such a liquid sample can be analyzed immediately, or at some future time. A plurality of such samples, each relating to a specific time period and/or location of collection, can be stored and later analyzed to quantitatively and/or qualitatively test for a specific particulate at a specific time. It is anticipated that such samples will be very useful in the study of potentially hazardous particulates, including but not limited to viruses, bacteria, bio-toxins, and pathogens. Those of ordinary skill in the art will readily recognize that such samples can be analyzed using a variety of known analytical techniques including, but not limited to, mass spectrophotometry.

In a simplest embodiment, the invention relates to method and means for removing concentrated spots of collected particulates from an impact collection surface, and transferring the removed particulates to a container suitable for a liquid sample. A jet of fluid can be utilized to remove and transfer the particulates to a container. When a liquid jet is employed, care should be taken to ensure that a minimal amount of liquid is utilized, to avoid unnecessarily diluting the resulting liquid sample. The fluid employed should be selected to be inert with respect to the collected particulates.

A mechanical scraper can alternatively be employed to remove and transfer the particulates to a suitable container. A small volume of liquid can be employed to rinse the scraper, again with the understanding that too much liquid would undesirably dilute the sample. It is contemplated that such a mechanical scraper can be vibrated to facilitate the removal of particulates from the scraper. Once transferred to a suitable container, the particulates can be stored dry (if no liquid has been employed in the removal and transfer processes), or a suitable (preferably small) volume of liquid can be used to prepare a liquid sample.

In some other embodiments, a portion of the collection surface containing a specific spot of particulates is removed and placed into a container. Again, once containerized, such a sample can be stored dry, or liquid can be added to the container to prepare a liquid sample.

Preferable containers are plastic, although glass, metal, and ceramic can also be employed. As with any sample container, exemplary containers will be inert and clean, so that no contaminants are introduced into the sample.

Other embodiments of the present invention relate to integrated systems, which include the impact collection surface as well. It is anticipated that the present invention will perform particularly effectively if fluid-entrained particulates (most often airborne particulates) are efficiently collected and concentrated, a task for which a virtual impactor, such as described in a commonly owned copending U.S. Patent Application entitled "ROBUST SYSTEM FOR SCREENING MAIL FOR BIOLOGICAL AGENTS." It is also particularly useful to providing means for moving the collection surface relative to the concentrated stream of particulates over time, so that spots located on different portions of the surface correspond to specific different increments of time. Preferably, the individual spots are disposed sufficiently far apart such that each individual spot can be removed and transferred to a suitable container without disturbing other spots.

The surface onto which the concentrated particulates are collected can be selected or modified to enhance the deposition of the particulates onto the surface, as well as to facilitate the removal and transfer of these particulates to a container suitable for preparing a liquid sample. In one embodiment, the impact collection surface is coated with a dissolvable coating, which is then rinsed with an appropriate solvent to remove the dissolvable coating and the collected particulates. In another embodiment, substantially the entire impact collection surface is soluble, and the portion of the impact collection surface with the desired spot of particles is removed and placed in the container. When the appropriate liquid (solvent) is added to the container, the collection surface dissolves and releases the particulates.

In another embodiment, the material of the collection surface is selected because of its porous nature. The pore sizes are sufficiently large to allow the fluid in which the particulates are entrained to freely pass through the archival surface, yet sufficiently small to prevent the particulates themselves from passing through the archival surface. Thus, the particulates are "filtered" from the fluid stream by the collection surface. To enhance removal of the particles, a fluid back flush can be employed. If the container is under a partial vacuum, the back flushed particles will be drawn into the container. Note that if the fluid is a gas, the concern regarding the use of so much liquid so as to undesirably dilute the sample of particles is obviated. In one embodiment, a vacuum is placed in fluid communication with an opposing side of a porous collection surface, causing the particles to adhere to the collection surface. When the vacuum source is no longer in fluid communication with the collection surface, the particles are readily removed.

In another embodiment, the collection surface is coated with a material selected to enhance a deposition of the particulates onto the collection surface while the material is in a first state, and to release the particulates when the material is in a second state. Such materials generally promote adhesion via chemical attraction, (i.e., a hydrophobic-hydrophobic attraction, or a hydrophilic-hydrophilic attraction). Electrical attraction can also be employed (i.e., a positively charged surface for collecting negative particles, or vice versa).

In at least one embodiment, the virtual impactor includes a separation plate employed for separating a fluid stream into a major flow and a minor flow. The major flow includes a minor portion of particles that are above a predetermined size, and the minor flow includes a major portion of the particles that are above the predetermined size. The separation plate includes a block in which is defined a laterally extending passage having an inlet disposed on one edge of the block and an outlet disposed on an opposite edge of the block. This laterally extending passage has a lateral dimension that is substantially greater than a transverse dimension of the passage. Opposed surfaces of the passage between which the transverse dimension of the passage is defined generally converge toward each other within the block, so that the outlet has a substantially smaller cross-sectional area than the inlet. A transverse, laterally extending slot is defined within the block and is in fluid communication with a portion of the passage that has the substantially smaller cross-sectional area. A major flow outlet port is also defined in the block, in fluid communication with the transverse, laterally extending slot. The major flow enters the slot and exits the block through the major flow outlet port, while the minor flow exits the block through the outlet of the passage. The major flow carries the minor portion of the particles and the minor flow carries the major portion of the particles.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1A is a schematic view of a virtual impactor;

FIG. 1B is a plan view of a separation plate employed in the present invention;

FIG. 1C is a cross-sectional view of the separation plate taken along line 1C—1C of FIG. 1B;

FIG. 1D is an enlarged view of a pair of a nozzle and a virtual impactor at section 1C of FIG. 1B;

FIG. 1E is an enlarged view of another configuration of a pair of a nozzle and a virtual impactor;

FIG. 2A is a schematic cross-sectional view of a virtual impact collector that includes another configuration of a separation plate in accord with the present invention;

FIG. 2B is a schematic perspective view of an alternative configuration of a virtual impact collector in accord with the present invention;

FIG. 3A is a plan view of a virtual impact collector incorporating plural pairs of a nozzle and a virtual impactor arranged radially;

FIG. 3B is a cross-sectional view of the virtual impact collector taken along line 3B—3B of FIG. 3A;

FIG. 4A is a plan view of another configuration of a separation plate in accordance with the present invention;

FIG. 4B is a cross-sectional view of the separation plate taken along line 4B—4B of FIG. 4A;

FIG. 4C is a cross-sectional view of the separation plate taken along line 4C—4C of FIG. 4A;

FIG. 5A is an isometric view of yet another alternative embodiment of a separation plate in accord with the present invention;

FIG. 5B is a cross-sectional view of the separation plate of FIG. 5A, showing additional separation plates arrayed on each side in phantom view;

FIG. 6A is an isometric view of still another alternative embodiment of a separation plate in accord with the present invention;

FIG. 6B is a cross-sectional view of the separation plate of FIG. 6A, showing additional separation plates arrayed on each side in phantom view;

FIG. 7 is a cross-sectional view of a separation plate like that shown in FIGS. 5A and 5B, but having a slightly modified passage through which the fluid flows to optimize the efficiency of separation over a broader range of particulate sizes;

FIG. 8 is a schematic view of a porous archival impaction surface in accord with one embodiment of the present invention;

FIG. 9 is a schematic view of a non-porous archival impaction surface in accord with another embodiment of the present invention;

FIG. 10 (prior art) is a schematic view of a fluid in which particulates are entrained, showing the particulates impacting an uncoated impact collection surface;

FIG. 11 is a schematic view of a fluid in which particulates are entrained, showing the particulates impacting a coated impact collection surface in accord with the present invention;

FIG. 12 is a schematic view of a flexible tape having a partially coated impact collection surface;

FIG. 13 is a schematic view of a flexible tape having a continuously coated impact collection surface;

FIG. 14 is a schematic illustration illustrating an impact collection surface coated with a material that includes antibodies selected to link with an antigen on a specific biological particulate;

FIGS. 15A and 15B illustrate two embodiments in which outwardly projecting structures are provided on an impact collection surface to enhance particulate collection;

FIG. 16 is an isometric view of a virtual impactor and an archival surface in accord with the present invention;

FIGS. 17A and 17B illustrate two embodiments of archival surfaces, each having a different pattern of archival spots; and FIG. 18A is a plan view of an exemplary ticket including two collection areas for use in an exemplary particle collection system;

Figure 23:
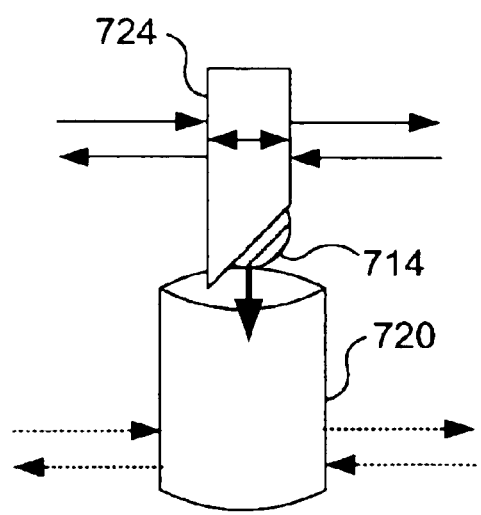
Figure 24A:
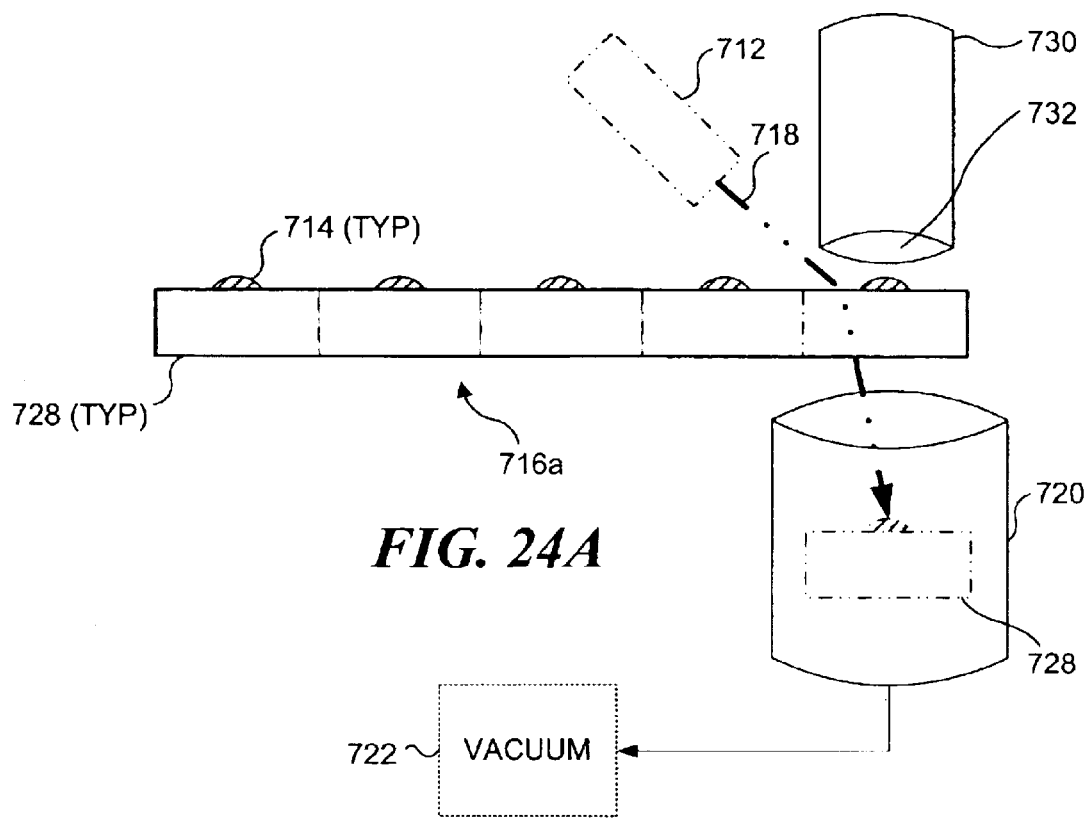
Figure 24B:
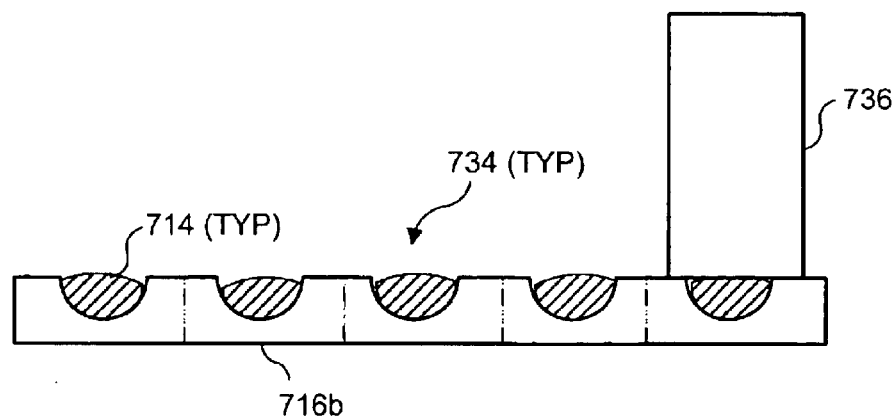

FIG. 23 is a block diagram of an embodiment in which a mechanical blade is vibrated to remove particles from the blade; and FIG. 24A is a block diagram of an embodiment in which a portion of a collection surface on which particles have been collected is removed and placed into a sample container; and FIG. 24B is a block diagram of an embodiment in which a portion of a collection surface that includes surface features into which particles have been collected is removed and placed into a sample container.

DESCRIPTION OF THE PREFERRED EMBODIMENTS

Overview of the Invention

The present invention is directed to a method and apparatus for removing concentrated samples or spots of collected particulates from an impact collection surface, and transferring the removed particulates to a container suitable for preparing a liquid sample. The sample can then be analyzed by any of a number of suitable techniques to identify the particulates that were collected. For example, such samples can be analyzed using mass spectrophotometry.

In a first embodiment, means are provided for removing and transferring the particulates from a collection surface into a sample container. This embodiment can be used with a variety of different impact collectors that collect the particulates on the collection surface.

Another embodiment includes elements for concentrating, collecting, and depositing "spots" of particulates from a fluid onto a collection surface, as well as the means for removing and transferring the particulates into a sample container. Such an integrated system can be employed to collect particulates, and facilitate preparation of a liquid sample. As noted above, many different analytical techniques require a liquid sample. While an impact collection surface might be removed from a separate system adapted to collect particulates and introduced into a separate system that is designed to prepare such a liquid sample, an integrated system that facilitates collection of the particulates and preparation of the liquid sample without removing the collection surface is preferable.

In one embodiment of an integrated system, the collection surface is an archival quality medium, preferably capable of retaining collected particulates in a stable environment for a relatively long period of time. Such a surface will function as an archive on which are deposited many spots collected at known temporally spaced-apart times from a known site. The archive will likely be useful if it is necessary to investigate environmental conditions at a particular site at a future time. Archived particulates can include, but are not limited to, viruses, bacteria, bio-toxins, and pathogens. When one or more spots from such an archive require analysis, the integrated system facilitates removal and transfer of the particulates to a sample container to provide a sample for analysis.

Preferably, such an integrated system employs a virtual impactor to efficiently collect and concentrate airborne particulates. The minor flow from the virtual impactor is directed toward a suitable archival quality surface to deposit concentrated spots of particulates. The archival surface is moved relative to the concentrated stream of particulates from the virtual impactor over time, so that spots or samples of the particulates that have been collected on different portions of the archival surface correspond to different times at which the particulates were collected. Preferably, the invention includes means for associating a date and time with each spot for the purpose of accurately archiving the sample collected, so that a specific spot can be located and retrieved.

A preferred integrated system also includes a control unit, such as a computing device or hard-wired logic device that executes sample protocols to determine when the fluid is sampled to produce each of the spots. Sample protocols can be applied to determine when a particular spot should be transferred from the collection surface to a sample container.

Those of ordinary skill in the art will recognize that other embodiments of an integrated system are possible within the scope of the present invention. For example, while it is deemed preferable to use a virtual impactor in such an integrated system, other types of particulate collectors can alternatively be employed.

In the following description, the prefix "micro" is applied generally to components that have sub-millimeter-sized features. Micro-components are fabricated using micro-machining techniques known in the art, such as micro-milling, photolithography, deep ultraviolet (or x-ray) lithography, electro-deposition, electro-discharge machining (EDM), laser ablation, and reactive or non-reactive ion etching. It should be noted that micro-machined virtual impactors provide for increased collection efficiency and reduced pressure drops.

Also as used hereinafter, the following terms shall have the definitions set forth below:

Particulate—any separately identifiable solid, semi-solid, liquid, aerosol, or other component entrained in a fluid stream that has a greater mass than the fluid forming the fluid stream, and which is subject to separation from the fluid stream and collection for analysis. For the purposes of the present description, the mass density of particulates is assumed to be approximately 1 gm/cm$^3$. It is contemplated that the particulates may arise from sampling almost any source, including but not limited to, air, water, soil, and surfaces, and may include inorganic or organic chemicals, or living materials, e.g., bacteria, cells, or spores.

Fluid—any fluid susceptible to fluid flow, which may comprise liquids or gases, and which may entrain foreign particulates in a flow thereof. Unless otherwise noted, fluid shall mean an ambient fluid containing unconcentrated particulates that are subject to collection, not the fluid into which the particulates are concentrated after collection or capture.

Spot—an aggregate of particulates deposited upon an archival surface in a relatively small area, so that the individually small particulates are aggregated together to form a larger spot, which can be more readily observed by magnification or by the naked eye.

The following description will first describe a preferred particulate collector and concentrator to be used in an integrated system. Then, archival surfaces for such an integrated system will be discussed, as well as suitable apparatus for moving the archival surface relative to the collector. Finally, suitable means for removing and transferring particulates from a collection surface to a container are discussed.

Particulate Concentrating

Because particulates of interest are often present in quite small concentrations in a volume of fluid, it is highly desirable to concentrate the mass of particulates into a smaller volume of fluid. Virtual impactors can achieve such a concentration without actually removing the particulates of interest from the flow of fluid. As a result, the particulate-laden fluid flow can be passed through a series of sequentially connected virtual impactors, so that a fluid flow exiting the final virtual impactor represents a concentration of particulates two to three orders of magnitude greater than in the original fluid flow. The concentrated particulates can then be more readily deposited on an archival surface.

Figure 1A:
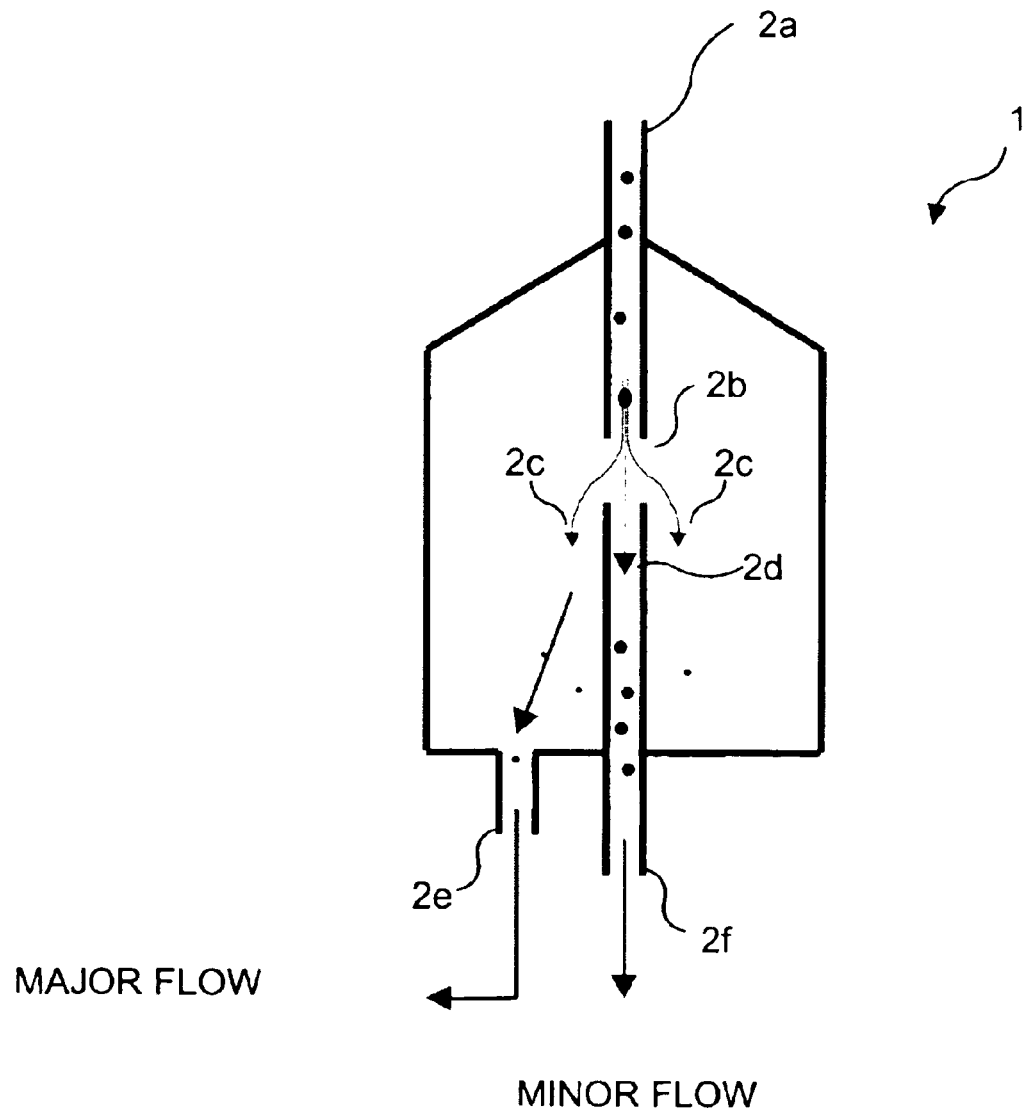

A virtual impactor uses a particle's inertia to separate it from a fluid stream that is turned, and a basic virtual impactor can be fabricated from a pair of opposing nozzles. Within a virtual impactor, the intake fluid coming through the inlet flows out from a nozzle directly at a second opposed nozzle into which only a "minor flow" is allowed to enter. This concept is schematically illustrated by a virtual impactor 1 shown in FIG. 1A. Fluid carrying entrained particulates flows through a first nozzle 2a. The flow from nozzle 2a then passes through a void 2b that separates nozzle 2a from a nozzle 2f. It is in void 2b that the flow of fluid is divided into a major flow 2c, which contains most of the fluid (e.g., 90%) and particles smaller than a cut (predetermined) size, and a minor flow 2d. Minor flow 2d contains a small amount of fluid (e.g., 10%) in which particulates larger than the cut size are entrained. Thus the minor flow exits via nozzle 2f, and the major flow exits via an outlet 2e.

As a result of inertia, most of the particulates that are greater than the selected cut size are conveyed in this small minor flow and exit the virtual impactor. Most of the particulates smaller than the virtual impactor cut size are exhausted with the majority of the inlet air as the major flow. The stopping distance of a particle is an important parameter in impactor design. The cut point (the size at which about 50% of the particles impact a surface, i.e., flow into the second nozzle) is related to the stopping distance. A 3 micron particle has nine times the stopping distance of a 1 micron particle of similar density.

For the present invention, several types of virtual impactors and their variants are suitable for use in collecting samples as spots for archiving purposes. Because any particular design of the minor flow nozzle can be optimized for a particular size of particles, it is contemplated that at least some embodiments of the present invention may include multiple nozzles, each with a different geometry, so that multiple particle types can be efficiently collected.

In one preferred embodiment, two virtual impactors are aligned in series, such that a concentration of particulates entrained in the minor flow of fluid exiting the second virtual impactor is approximately 100 times the original concentration.

Figure 1B:
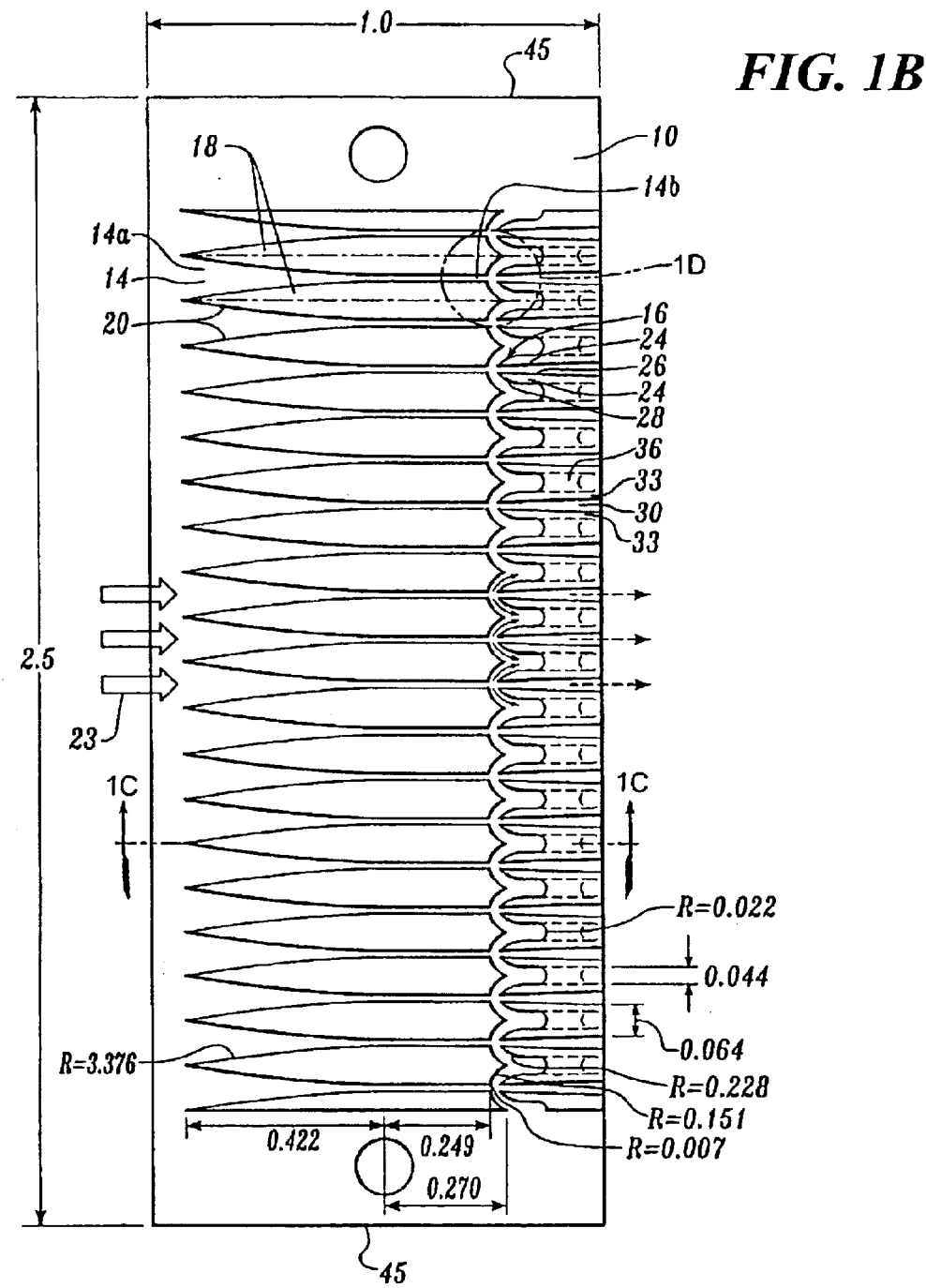
Figure 1C:
Figure 1D:
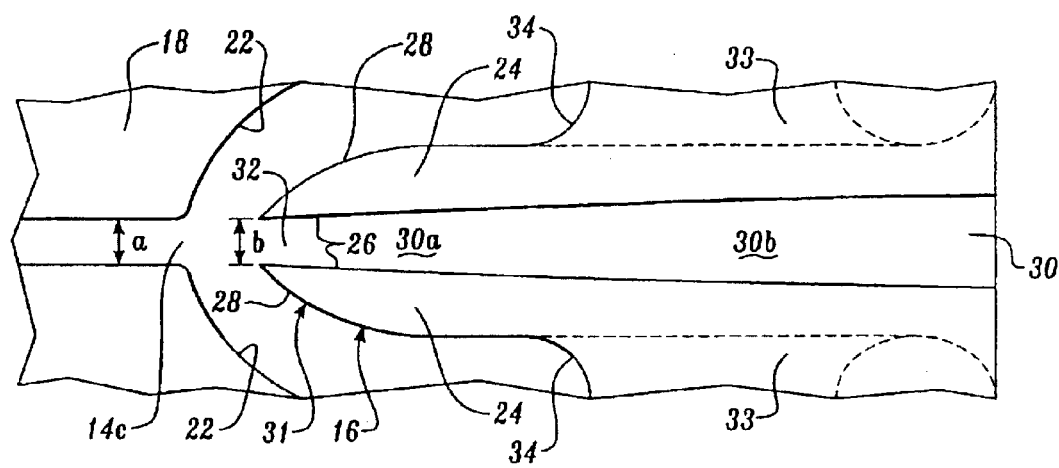

FIGS. 1B, 1C, and 1D illustrate a first embodiment of a virtual impact separation plate 10 formed in accordance with the present invention. Separation plate 10 may be formed of various materials suitable for micro-machining, such as plastics and metals. The separation plate includes a first surface 10a and an opposing second surface 10b (FIG. 1C). The first surface 10a includes plural pairs of a nozzle 14 and a virtual impactor 16 (FIG. 1D). Each nozzle 14 includes an inlet end 14a and an outlet end 14b and is defined between adjacent nozzle projections 18 having a height "H" (see FIG. 1C). Two nozzle projections 18 cooperate to define one nozzle 14. Each nozzle projection 18 includes two side walls 20 that are configured to define one side of a nozzle 14, which comprise a telescoping design that generally tapers from inlet end 14a to outlet end 14b. Nozzle projection 18 further includes two generally concave walls 22 at its downstream end that are positioned to provide nozzle projection 18 with a tapered downstream "tail." In contrast to a tapered downstream tail, another of the embodiments described below that is actually more preferred includes stepped transitions that reduce the size of the passage at its outlet. Throughout the present description, the terms "upstream" and "downstream" are used to refer to the direction of a fluid stream 23 flowing through the separation plate of the present invention.

Each virtual impactor 16 comprises a pair of generally fin-shaped projections 24 having height "H." Each fin-shaped projection 24 includes an inner wall 26 and a generally convex outer wall 28. Inner walls 26 of fin-shaped projections 24 (for a pair) are spaced apart and face each other to define an upstream minor flow passage 30a there between. Convex outer walls 28 of the pair of fin-shaped projections 24 cooperatively present a generally convex surface 31 facing the fluid flow direction. Referring specifically to FIG. 1D, an inlet end 32 of upstream minor flow passage 30a defines a virtual impact void through convex surface 31, where "virtual" impaction occurs as more fully described below. A width of outlet end 14b of nozzle 14 is defined as "a," and a width of inlet end 32 of upstream minor flow passage 30a is defined as "b."

First surface 10a of separation plate 10 may further include a plurality of virtual impactor bodies 33 extending downstream from the downstream ends of adjacent fin-shaped projections 24 of adjacent pairs of virtual impactors 16. Each virtual impactor body 33 includes opposing external walls that extend downstream from the downstream ends of inner walls 26. External walls of adjacent virtual impactor bodies 33 are spaced apart to define a downstream minor flow passage 30b there between. Upstream and downstream minor flow passages 30a and 30b are aligned and communicate with each other to form minor flow passage 30. As illustrated in FIGS. 1B, 1C, and 1D, fin-shaped projections 24 of adjacent virtual impactors 16 and virtual impactor body 33 may be integrally formed. Optionally, an orifice 34 may be defined through virtual impactor body 33 adjacent to the downstream ends of convex outer walls 28 of adjacent virtual impactors 16. Orifices 34 define terminal ends of passageways 36 that extend downwardly and downstream through separation plate 10 to second surfaces 10b. As more fully described below, orifices 34 and passageways 36 are provided merely as one example of a major flow outlet and, thus, may be replaced with any other suitable major flow outlet.

In operation, particulate-laden fluid stream 23 is caused to enter inlet ends 14a of nozzles 14. Nozzles 14 aerodynamically focus and accelerate particulates entrained in fluid stream 23. In this telescoping design, the aerodynamically focused fluid stream 23 exiting outlet ends 14b of nozzles 14 advances to convex surfaces 31 of virtual impactors 16. A major portion (at least 50%, and preferably, at least about 90%) of fluid stream 23 containing a minor portion (less than about 50%) of particulates above a certain particulate diameter size, or a cut size, hereinafter referred to as a "major flow," changes direction to avoid the obstruction presented by convex surfaces 31. Concave walls 22 of nozzle projections 18 and convex outer walls 28 of fin-shaped projections 24 cooperate to direct the major flow toward the upstream end of virtual impactor bodies 33. Bodies 33 prevent the major flow from continuing in its current direction. Orifices 34 are provided through bodies 33, so that the major flow enters orifices 34 and travels through passageways 36 to second surface 10b of separation plate 10, where it is exhausted or processed further. A minor portion (less than 50%, and preferably less than about 10%) of fluid stream 23 containing a major portion (at least about 50%) of particulates above the cut size, exits as the minor flow and is collected near a "dead" zone or a zone of nearly stagnant air created adjacent to the convex surfaces 31 of virtual impactors 16. The major portion of the particulates entrained in the minor flow "virtually" impacts the virtual impact voids at inlet ends 32 of upstream minor flow passages 30a and enters minor flow passages 30. The minor flow travels through and exits minor flow passages 30, enabling the particulates entrained therein to be collected for analysis and/or further processing.

Nozzles 14 contribute very little to particulate loss because they have a long telescoping profile, which prevents particulate deposition thereon. The long telescoping profile of the nozzles 14 also serves to align and accelerate particulates. Focusing the particulates before they enter the minor flow passage using the telescoping design may enhance the performance of the virtual impactor, since the particulates in the center of the nozzle are likely to remain entrained in the minor flow. Thus, as used herein, the term "aerodynamic focusing" refers to a geometry of a particulate separator that concentrates particulates toward the center of a central channel through the particulate separator. Because nozzles 14 aerodynamically focus and accelerate particulates in a fluid stream, virtual impactors 16 placed downstream of nozzles 14 are able to separate particulates very efficiently. By improving the particulate separation efficiency of each of virtual impactors 16, the present invention enables only one layer or row of virtual impactors 16 to carryout the particulate separation, which eliminates the chances of particulates being lost due to impact on surfaces of additional layers or rows of virtual impactors. The present invention further reduces particulate loss on inner surfaces of minor flow passages, by enabling minor flows to advance straight through the minor flow passages upon virtual impaction, without having to change their flow direction.

A separation plate 10 configured in accordance with the dimensions (all in inches) shown in FIGS. 1B and 1C is designed to have a cut size of about 1.0 microns at a flow rate of 35 liters per minute (1 pm). It should be understood that those of ordinary skill in the art may readily optimize separation plate 10 of the present invention to meet a specific cut size requirement at a predefined flow rate. For example, the cut size of a separation plate may be modified by scaling up or down the various structures provided on the separation plate; larger nozzles with proportionally larger virtual impactors are useful in separating larger particulates, while conversely, smaller nozzles with proportionally smaller virtual impactors are useful in separating smaller particulates. The cut size of a separation plate may also be modified by adjusting a flow rate through the separation plate.

With reference to FIG. 1D, for particulates having 1 to 3 micron diameters, it has been found that making the dimension "a" greater than the dimension "b" generally reduces recirculation of a minor flow upon entering minor flow passage 30, which is preferable for efficiently separating a minor flow from a major flow. For larger particulates, it may be preferable to make "b" larger than "a" to reduce pressure drop.

Figure 1E:
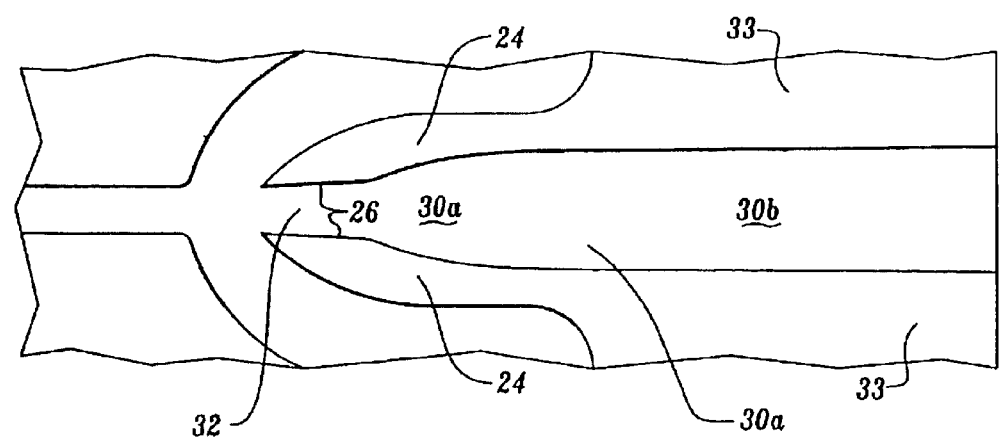

FIG. 1E illustrates modified configurations of a nozzle 14 and a virtual impactor 16, wherein inner walls 26 of fin-shaped projections 24 include a generally concave surface. Accordingly, the width of upstream minor flow passage 30a expands from inlet end 32 toward downstream minor flow passage 30b, which is defined between the external walls of adjacent virtual impactor bodies 33. This configuration is advantageous in reducing particulate loss onto inner walls 26.

A separation plate of the present invention may be easily modified to process virtually any volume of fluid stream at any flow rate, by varying the number of nozzles 14 and virtual impactors 16 provided on the separation plate. Furthermore, the throughput of separation plate 10 may be almost indefinitely modifiable by increasing or decreasing height "H" of nozzles 14, virtual impactors 16, and virtual impactor bodies 33. It should be noted that height "H" of a separation plate of the invention could be freely increased without a significant increase in particulate loss. This capability is made possible by the design of this virtual impactor that allows minor flows to advance straight through without experiencing any deflected path.

Figure 2A:
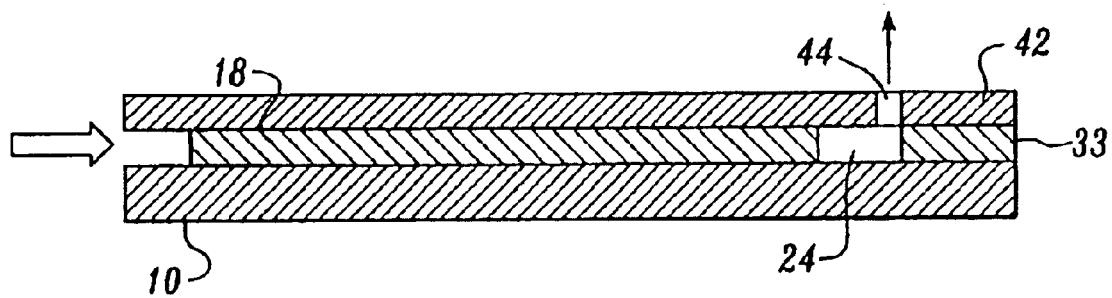

Separation plate 10 of the present invention may be readily incorporated into various particulate separation/ concentration apparatus. Referring to FIG. 2A, for example, a virtual impact collector may be formed by placing a cover plate 42 over projections 18, fin-shaped projections 24, and virtual impactor bodies 33 provided on first surface 10a. Cover plate 42 and first surface 10a cooperatively define a chamber. Inlet ends 14a of nozzles 14 provide an inlet through which a particulate-laden fluid stream may enter the chamber. Minor flow passages 30 provide an outlet through which a minor flow may exit the chamber; however, an outlet through which a major flow may exit the chamber may be provided in various other ways. For example, as in FIGS. 1B and 1C, the plurality of orifices 34 defining terminal ends of passageways 36 may be provided through virtual impactor bodies 33. Alternatively, as in FIG. 2A, cover plate 42 may include a plurality of orifices 44 that extend there through. Orifices 44 are configured and arranged so that when cover plate 42 is mated with separation plate 10, orifices 44 are disposed between virtual impactors 16 and adjacent to the upstream end of virtual impactor bodies 33, to exhaust major flows flowing around virtual impactors 16 that are blocked by bodies 33, as indicated by the arrow. It should be understood that, in operating the virtual impact collector as described above, those of ordinary skill in the art can provide a suitable flow subsystem for causing a fluid stream to flow through the chamber.

Figure 2B:
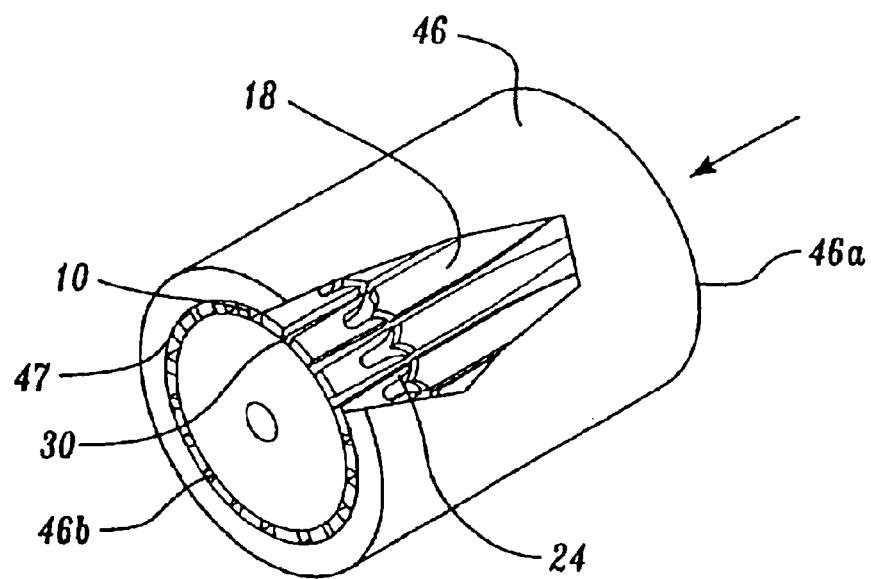

A further example of a virtual impact collector formed in accordance with the present invention is schematically illustrated in FIG. 2B. In this embodiment, separation plate 10 of FIG. 1B is joined at its opposing edges 45 to form a cylinder. The second surface of separation plate 10 forms the inner surface of the cylinder. The cylindrical separation plate 10 is coaxially slid into a tube 46 having two open ends 46a and 46b to form an annular chamber 47 there between. As before, a suitable major flow outlet (not shown) is provided. In operation, particulate-laden fluid streams enter chamber 47 through the inlet ends of the nozzles defined between nozzle projections 18, adjacent to open end 46a. Minor flow passages 30 provide an outlet through which a minor flow exits chamber 47. A suitably provided major flow outlet deflects a major flow to either or both of the inner surfaces of the cylindrical separation plate 10 and/or the outer surface of tube 46.

Figure 3A:
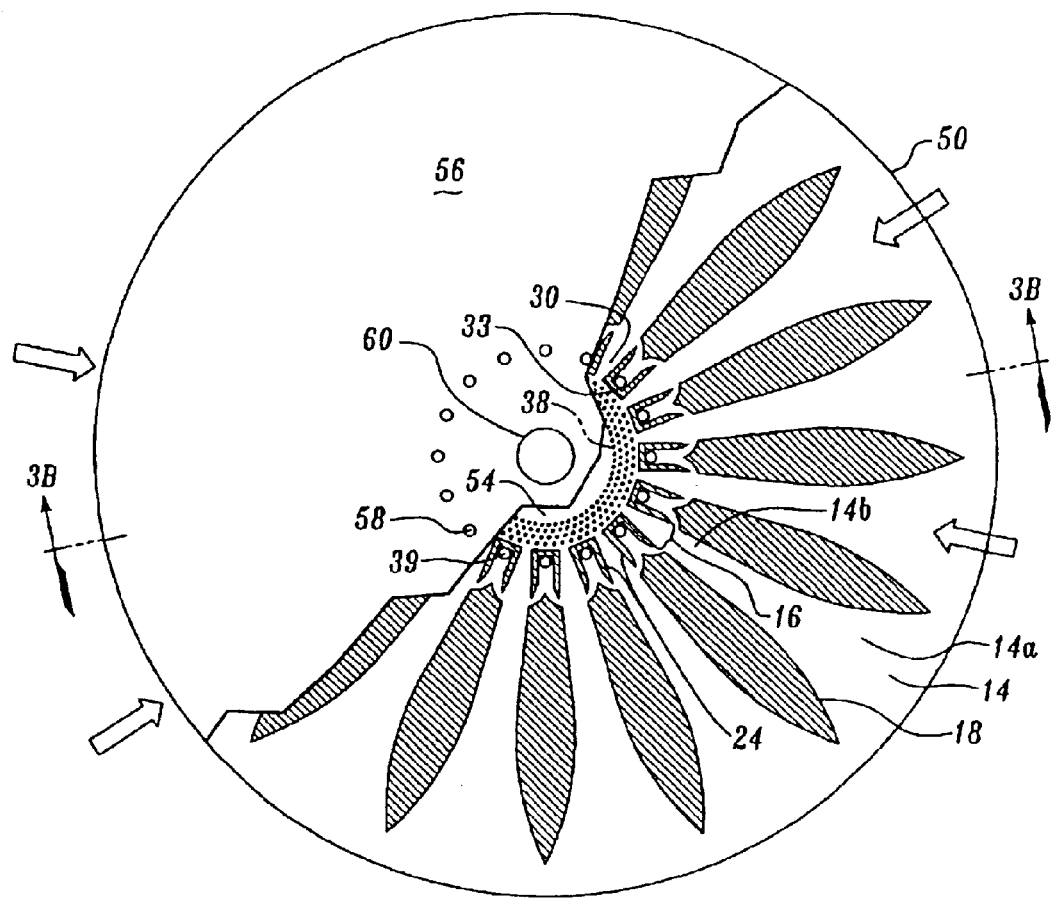
Figure 3B:
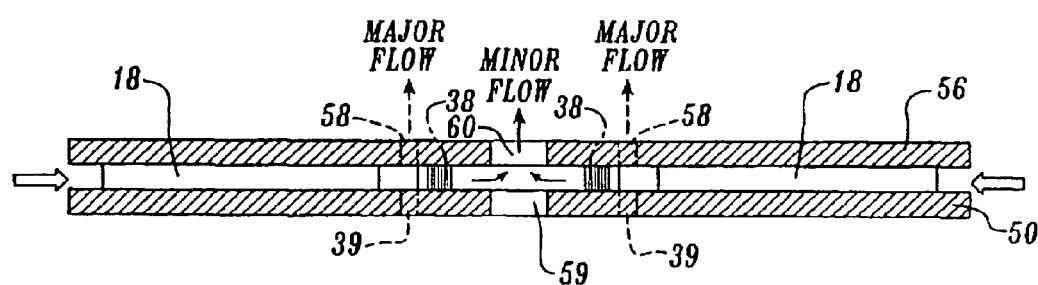
Figure 4A:
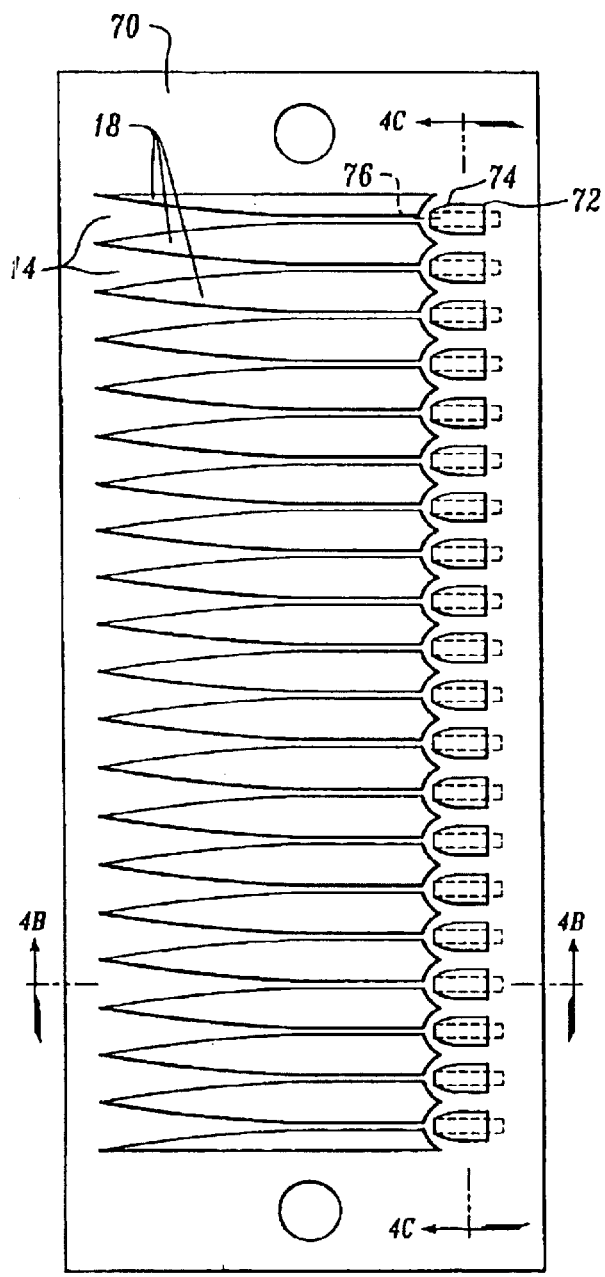
Figure 4C:
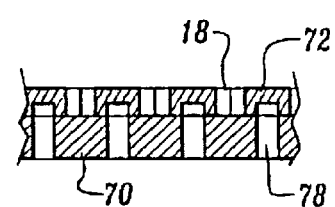
Figure 4B:
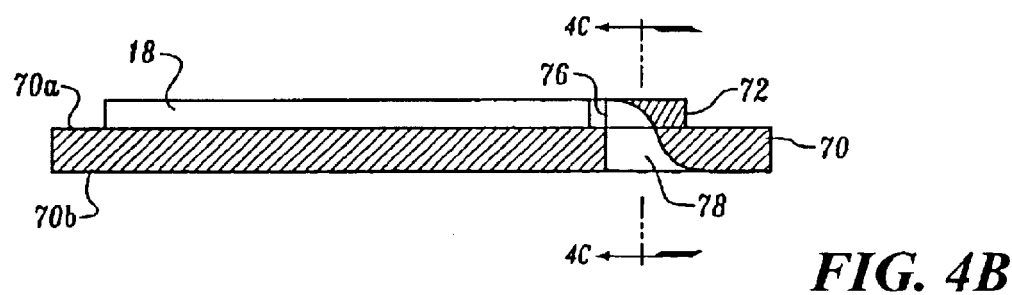

FIGS. 3A and 3B schematically illustrate a radial virtual impact collector including a separation plate 50 and a cover plate 56, in accord with the present invention. Separation plate 50 includes plural pairs of nozzles 14 and virtual impactors 16; the virtual impactors are disposed radially inward of nozzles 14. As before, nozzle 14, which has an inlet end 14a and an outlet end 14b, is defined between adjacent nozzle projections 18. Virtual impactor 16 comprises a pair of fin-shaped projections 24 disposed downstream and radially inward of outlet end 14b of each nozzle 14. As before, fin-shaped projections 24 in each pair are spaced apart and define minor flow passage 30 there between. Also as before, a plurality of virtual impactor bodies 33 in the form of a wall extend between the downstream ends of fin-shaped projections 24 of adjacent virtual impactors 16. A plurality of orifices 39 are provided through separation plate 50 radially outward of virtual impactor bodies 33 and between fin-shaped projections 24 of adjacent virtual impactors 16. Virtual impactors 16 and bodies 33 together define a central minor flow collection portion 54. A plurality of impactor pillars 38 are disposed radially inward and downstream of minor flow passages 30, within central minor flow collection portion 54. Impactor pillars 38 are employed to receive a minor flow and to collect particulates thereon, as more fully described below. A minor flow outlet 59 is provided through separation plate 50 near the center of central minor flow collection portion 54. Separation plate 50, which is described above, may be combined with cover plate 56 to form the virtual impact collector. Cover plate 56 is configured to mate with separation plate 50 to define a chamber there between. Cover plate 56 optionally include holes 58 that are configured and arranged so that when separation plate 50 and cover plate 56 are combined, holes 58 are aligned to coincide with holes 39 defined through separation plate 50. Optionally, cover plate 56 may include a minor flow outlet 60 defined there through. Minor flow outlet 60 is configured so that when cover plate 56 and separation plate 50 are combined, minor flow outlet 60 of cover plate 56 aligns with minor flow outlet 59 of separation plate 50. Holes 39 of separation plate 50 and/or holes 58 of cover plate 56 provide a major flow outlet to the chamber. Minor flow outlet 59 of separation plate 50 and/or minor flow outlet 60 of cover plate 56 provide a minor flow exhaust to the chamber.

In operation, particulate-laden fluid streams enter nozzles 14 through inlet ends 14a and advance radially inward. When aerodynamically focused fluid streams advance toward virtual impactors 16, they are separated into a minor flow and a major flow, as described above. The major flow flows around virtual impactors 16, is redirected by bodies 33, and is exhausted through either or both of holes 39 in separation plate 50 and/or holes 58 in cover plate 56. The minor flow advances through minor flow passages 30 into central minor flow collection portion 54. When impactor pillars 38 are provided, some of the particulates entrained in the minor flow may impact and become deposited on impactors 38. The particulates collected on impactor pillars 38 may be subsequently collected, for example, by washing impactor pillars 38 with a small amount of liquid to capture the particulates therein. An example of impactors suitable for use in conjunction with the present invention can be found in copending U.S. patent application Ser. No. 09/191,979, filed Nov. 13, 1998, concurrently with the parent case hereof, and assigned to the same assignee, which is herein expressly incorporated by reference. The minor flow may be exhausted from central minor flow collection portion 54 through either or both of minor flow outlets 59 and 60.

When both minor flow outlets 59 and 60, and both holes 39 and 58 are provided, as illustrated in FIG. 3B, a plurality of the virtual impact collectors described above may be stacked together to process large amounts of fluid streams. The stacked virtual impact collectors include a common minor flow exhaust conduit comprising minor flow outlets 59 and 60, and a common major flow exhaust conduit comprising holes 39 and 58.

FIGS. 4A, 4B, and 4C illustrate another embodiment of a separation plate 70 in accordance with the present invention. As in the first embodiment, separation plate 70 includes a first surface 70*a* and an opposing second surface 70*b*. First surface 70*a* is provided with a plurality of nozzle projections 18 that define nozzles 14 there between. As before, nozzle 14 tapers from an inlet end 14*a* to an outlet end 14*b*. Downstream of each outlet end 14*b*, a generally haystack-shaped virtual impactor projection 72 is provided. Virtual impactor projection 72 includes a convex leading surface 74 facing the fluid flow. A virtual impact void 76 is provided through convex surface 74 near its apex. Virtual impact void 76 defines a terminal end of a minor flow passage 78 that extends down and through separation plate 70. Minor flow passage 78 and virtual impact void 76 may be formed by, for example, boring an end-mill through second surface 70*b* of separation plate 70. Alternatively, minor flow passage 78 and virtual impact void 76 may be formed by drilling a hole through separation plate 70. When drilling a hole, minor flow passage 78 preferably passes through separation plate 70 at an acute angle so that a minor flow containing a major portion of particulates will avoid sharp changes in direction upon entering virtual impact void 76. It should be noted that the longer minor flow passage 78, the more particulates may be deposited on the inner surfaces of minor flow passage 78. Therefore, while the angle of minor flow passage 78 should be as acute as possible, the length of minor flow passage 78 cannot be indefinitely long. The optimum combination of the angle and the length of minor flow passage 78 is to be determined based partly on the limitations imposed by the available micro-machining methods. An angle of between approximately 15° and 45°, which is possible with currently available micro-machining methods, should provide satisfactory results.

In operation, particulate-laden fluid streams flow along first surface 10*a* through nozzles 14 and advance toward convex surfaces 74 of virtual impactor projections 72. Major flows continue around projections 72 to avoid obstruction presented by convex surfaces 74, and flow along first surface 10*a*. Minor flows are collected in a zone of stagnant fluid created near convex surfaces 74, and enter virtual impact voids 76 defined through convex surfaces 74. The minor flows travel through minor flow passages 78 to second surface 70*b*, where they can be collected, and analyzed or processed after being archived, as discussed below. Thus, unlike separation plates 10 and 50 of the previous embodiments, separation plate 70 of the present embodiment separates a particulate-laden fluid stream into a minor flow on the second surface, and a major flow on the first surface.

Figure 5A:
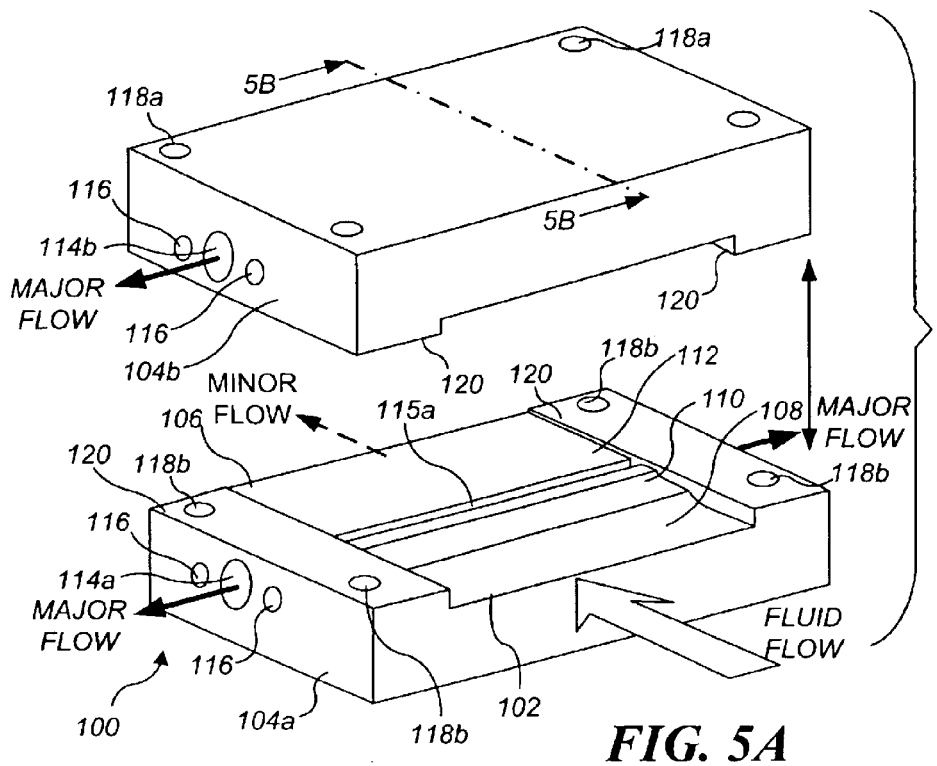
Figure 5B:
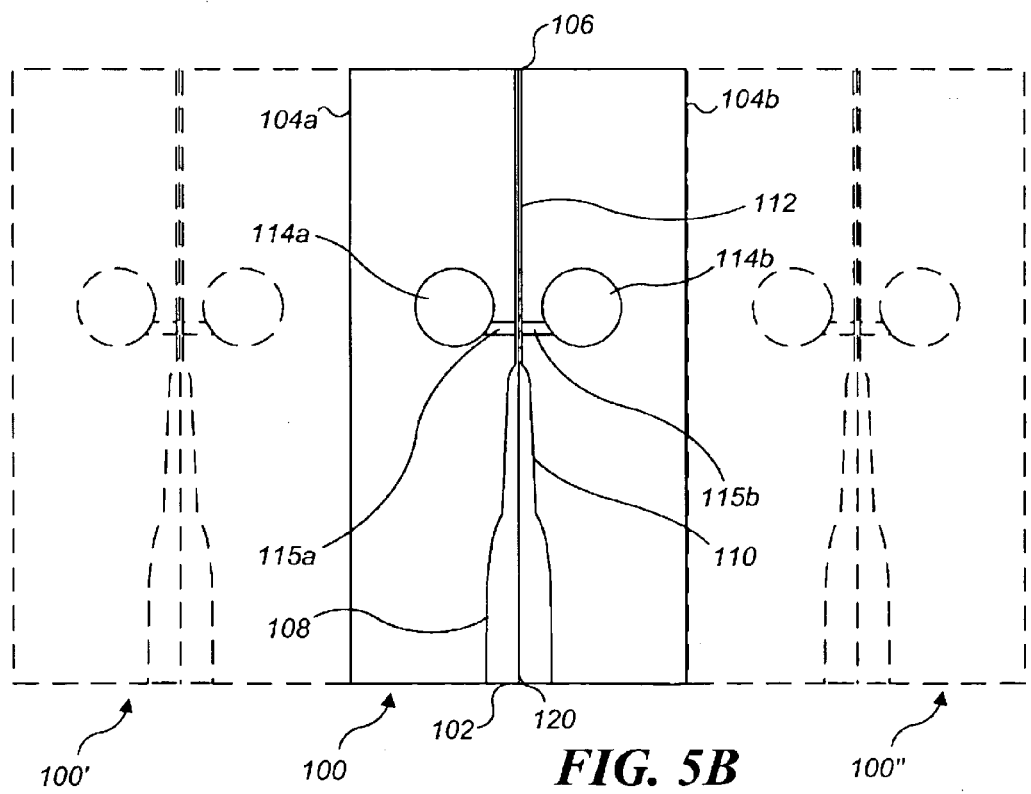

Another embodiment of a separation plate 100 is illustrated in FIGS. 5A and 5B. A separation plate 100 includes a central passage 102 that extends laterally across the length of the separation plate and through its width. The passage is defined between plates 104*a* and 104*b* and is machined within the facing surfaces of these two plates, which preferably comprise a metal such as steel, aluminum, or titanium, or a another suitable material such as plastic. Alternatively, the passage can be formed by molding or casting the plates from metal, or another suitable material, such as plastic. Passage 102 is readily formed in the surfaces of each of plates 104*a* and 104*b* by conventional machining techniques. Since the surfaces are fully exposed, the desired telescoping or converging configuration of the passage is readily formed. The passage extends from an inlet 108, which is substantially greater in cross-sectional area due to its greater height compared to that of an outlet 106. The outlet is disposed on the opposite side of the separation plate from the inlet. Inlet 108 tapers to a convergent nozzle 110, which further tapers to the opening into a minor flow portion 112 of passage 102.

In this preferred embodiment of separation plate 100, one-half of the thickness of passage 102 is formed in plate 104*a*, and the other half of the thickness of the passage is formed in plate 104*b*. However, it is also contemplated that the portions of the passage defined in each of plates 104*a* and 104*b* need not be symmetrical or identical, since a desired configuration for passage 102 can be asymmetric relative to the facing opposed surfaces of the two plates.

Immediately distal of the point where minor flow portion 112 of passage 102 begins, slots 115*a* and 115*b* are defined and extend transversely into the plates relative to the direction between the inlet and the outlet of passage 102 and extend laterally across separation plate 100 between the sides of the passage. Slots 115*a* and 115*b* respectively open into major flow outlet ports 114*a* and 114*b* in the ends of plates 104*a* and 104*b*, as shown in FIG. 5A. Threaded fastener holes 116 are disposed on opposite sides of each of major flow outlet ports 114*a* and 114*b* and are used for connecting a major flow manifold (not shown) that receives the major flow of fluid in which the minor portion of the particulates greater than the cut size is entrained.

Fastener holes 118*a* are formed through plate 104*b* adjacent to its four corners and do not include threads. Threaded fasteners (not shown) are intended to be inserted through holes 118*a* and threaded into holes 118*b*, which are formed at corresponding corner positions on plate 104*a*. The threaded fasteners thus couple edge seals 120 on the two plates together, sealing the edges of passage 102 and connecting plates 104*a* and 104*b* to form separation plate 100. Although not shown, a manifold may also be connected to the back surface of separation plate 100 overlying outlet 106 to collect the minor flow of fluid in which the major portion of particulates exceeding the cut size is entrained. In FIG. 5A, the flow of fluid entering inlet 108 of passage 102 is indicated by the large arrow, the major flow exiting major flow ports 114*a* and 114*b* is indicated by the solid line arrows, and the minor flow exiting outlet 106 of passage 102 is indicated by the dash line arrow. The cross-sectional profile of passage 102 as shown in FIG. 5B focuses the particulate-laden fluid flow entering inlet 106 for delivery to the receiving nozzle and thus performs in much the same way as the profile used in the previous embodiments of virtual impactors.

The desired flow through the separation plate will determine the width of passage 102, as measured along the longitudinal axis of the separation plate, between sealed edges 120. Additional fluid flow can also be accommodated by providing a plurality of the separation plates in an array, which will also avoid using extremely long and thin structures that may not fit within an available space. FIG. 5B illustrates two such additional separation plates 100' and 100", stacked on each side of separation plate 100, so that the fluid enters the inlets of the stacked separation plates and is separated in the major flow and the minor flow exiting the separation plates, as described above.

FIGS. 6A and 6B illustrate still another embodiment of a separation plate 200 that is similar to separation plate 100, which was discussed above in regard to FIGS. 5A and 5B. Separation plate 200 differs from separation plate 100 in at least two significant ways, as will be apparent from the following discussion. To simplify the following explanation of separation plate 200, the reference numbers applied to its elements that are similar in function to those of separation plate 100 are greater by 100. Thus, like central passage 102 in separation plate 100, separation plate 200 includes a central passage 202 that extends laterally across the length of the separation plate and through its width. The passage is defined between plates 204*a* and 204*b* and is machined within the facing surfaces of these two plates, which also preferably comprise a metal such as steel, aluminum, or titanium formed by machining or by molding the plates from metal, or another suitable material, such as a plastic. The passage extends from an inlet 208, which is substantially greater in cross-sectional area due to its greater height, to an outlet 206 disposed on the opposite side of the separation plate from the inlet. Unlike inlet 108 of the previous embodiment, which tapers to a convergent nozzle 110 and then to a minor flow portion 112 of passage 102, the central passage in separation plate 200 does not taper to smaller cross-sectional sizes. Instead, the central passage in separation plate 200 changes abruptly to a smaller cross-sectional size at a step 222, continuing through a section 210, and then again decrease abruptly to a smaller minor flow outlet 212, at a step 224. At each of steps 222 and 224, a swirling flow or vortex 226 of the fluid is produced. It has been empirically determined that these vortexes tend to focus the particulates toward the center of the passage, thereby providing a substantial improvement in the efficiency with which the particulates smaller than the cut size are separated from the particulates larger than the cut size.

In this preferred embodiment of separation plate 200, one-half the thickness of passage 202 is formed in plate 204*a*, and the other half of the thickness of the passage is formed in plate 204*b*, just as in the previous embodiment. Again, it is contemplated that the portions of the passage defined in each of plates 204*a* and 204*b* need not be symmetrical or identical, since a desired configuration for passage 202 can be asymmetric relative to the facing opposed surfaces of the two plates.

Immediately distal of the point where minor flow portion 212 of passage 202 begins, slots 215*a* and 215*b* are defined and extend transversely into the plates relative to the direction between the inlet and the outlet of passage 202 and extend laterally across separation plate 200 between the sides of the passage, just as in separation plate 100. Slots 215a and 215b respectively open into major flow outlet ports 217a and 217b, which are open to the ends and outer surfaces of plates 204a and 204b, as shown in FIG. 6A. In this embodiment, separation plate 200 is designed to be stacked with other similar separation plates 200' and 200", as shown in FIG. 6B, so that adjacent separation plates cooperate in forming the passage for conveying the major flow into an overlying major flow manifold (not shown). It is also contemplated that separation plate 100 can be configured to include major flow outlet ports similar to those in separation plate 200. The last plate disposed at the top and bottom of a stack of separation plates configured like those in FIG. 6B would include major flow outlet ports 114a and 114b, respectively. Threaded fastener holes 216 are disposed on opposite sides of each of major flow outlet ports 217a and 217b and are used for connecting a major flow manifold (not shown) that receives the major flow of fluid in which the minor portion of the particulates greater than the cut size is entrained.

Fastener holes 218a are formed through plate 204b adjacent to its four corners and do not include threads. Threaded fasteners (not shown) are intended to be inserted through holes 218a and threaded into holes 218b, which are formed at corresponding corner positions on plate 204a. The threaded fasteners thus couple edge seals 220 on the two plates together, sealing the edges of passage 202 and connecting plates 204a and 204b to form separation plate 200. Although not shown, a manifold may also be connected to the back surface of separation plate 200 overlying outlet 206 to collect the minor flow of fluid in which the major portion of particulates exceeding the cut size is entrained, for use in creating an archive of the samples thus collected as explained below. In FIG. 6A, the flow of fluid entering inlet 208 of passage 202 is indicated by the large arrow, the major flow exiting major flow outlet ports 217a and 217b is indicated by the solid line arrows, and the minor flow exiting outlet 206 of passage 202 is indicated by the dash line arrow.

Separation plates 100 and 200 costs less to manufacture than the other embodiments discussed above. As was the case with separation plate 100, the desired flow through the separation plate will determine the width of passage 202 along the longitudinal axis of the separation plate, between sealed edges 220, and additional fluid flow can also be accommodated by providing a plurality of the separation plates in an array configured to fit within an available space. FIG. 6B illustrates two additional separation plates 200' and 200", stacked on opposite sides of separation plate 200, so that the fluid enters the inlets of the stacked separation plates and is separated in the major flow and the minor flow exiting the separations plates, as described above.

Figure 7:
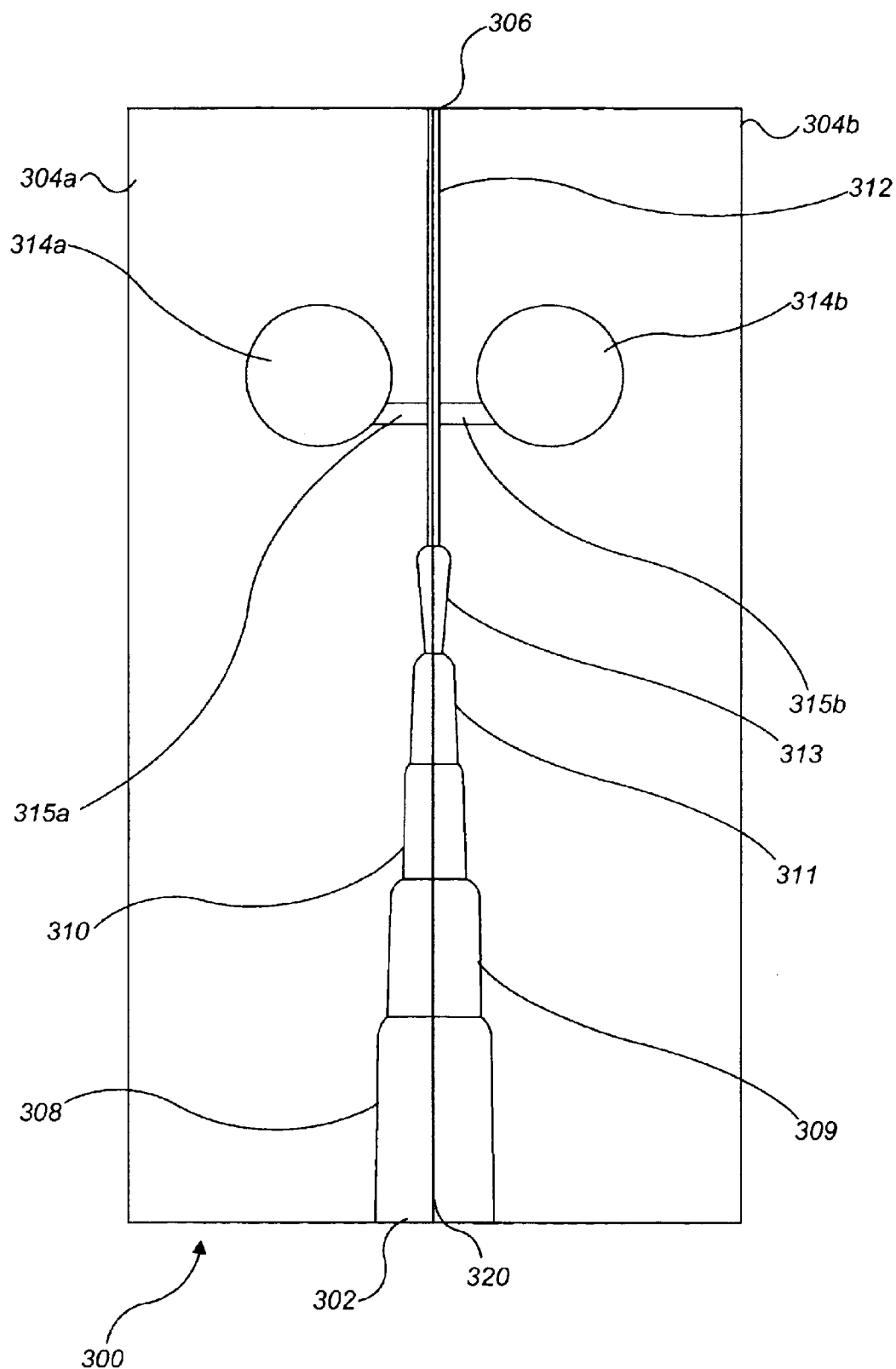
Figure 8:
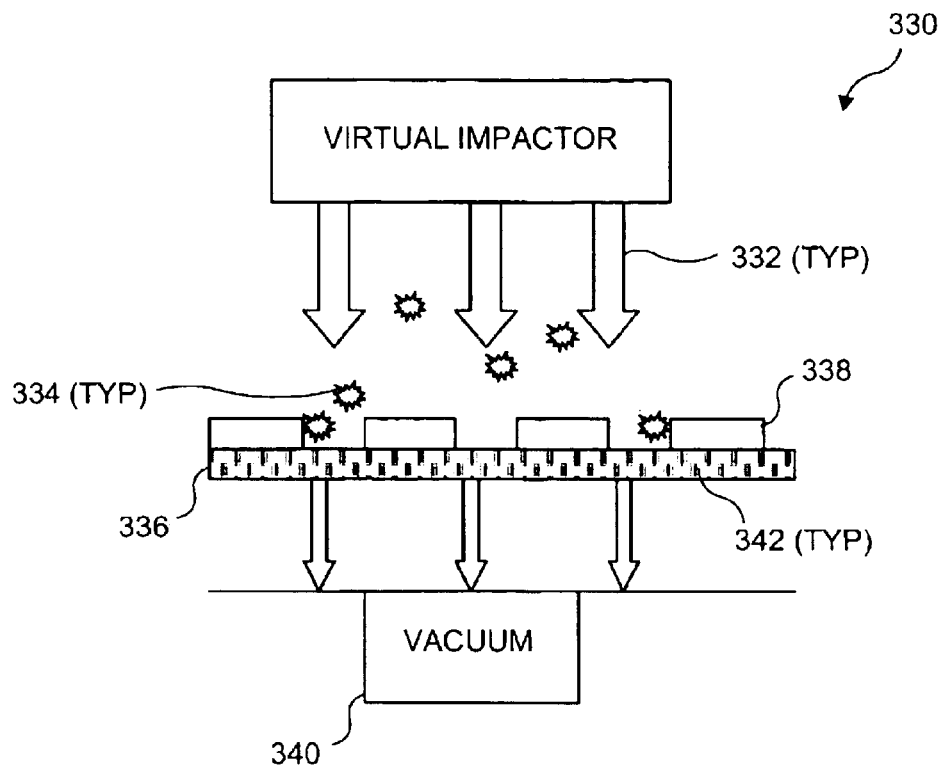
Figure 9:
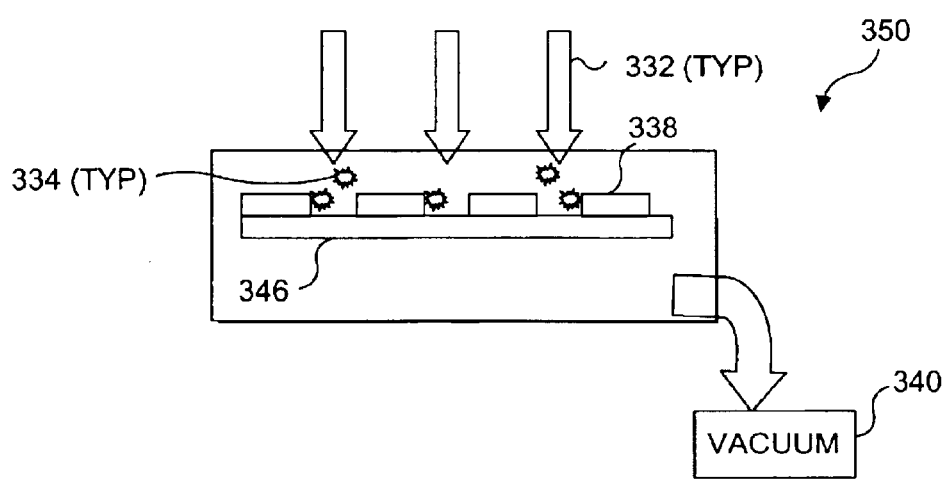
Figure 10:
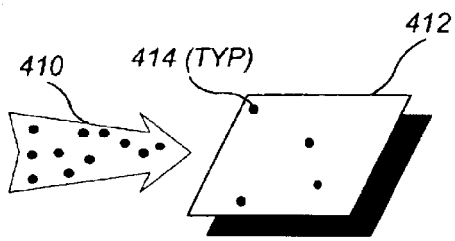
Figure 11:
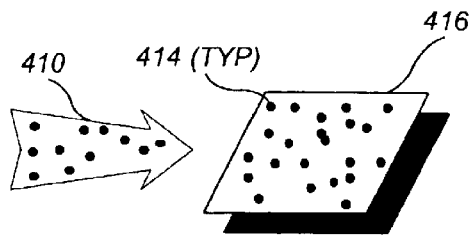

Finally, yet another embodiment of the present invention, a separation plate 300 is illustrated in FIG. 7. Separation plate 300 is also similar to separation plate 100, which is shown in FIGS. 5A and 5B, but includes a central passage 302 that differs from central passage 102 in separation plate 100. Again, to simplify the following explanation, reference numbers applied to the elements of separation plate 300 that are similar in function to those of separation plate 100 are greater by 200. It will thus be apparent that central passage 102 in separation plate 100 corresponds to central passage 302 in separation plate 300 and that central passage 302 extends laterally across the length of separation plate 300 and through its width. The passage is defined between plates 304a and 304b and is machined within the facing surfaces of these two plates, preferably from a metal such as steel, aluminum, or titanium formed by machining, or by molding the plates from metal, or another suitable material, such as a plastic. The passage extends from an inlet 308, which is substantially greater in cross-sectional area due to its greater height, to an outlet 306 disposed on the opposite side of the separation plate from the inlet. Central passage 302 comprises a telescoping section that performs aerodynamic focusing of the particulates so as to achieve a further optimization in maximizing the efficiency of the separation plate over a wider range of particulates sizes, compared to the other embodiments. The focusing is accomplished in this embodiment by using a combination of contracting and diverging sections. Specifically, an inlet 308 tapers slightly at its distal end to a more convergent section 309, which again tapers to a convergent nozzle 310, which further tapers at its distal end to another convergent section 311. The distal end of convergent section 311 tapers into the proximal end of a divergent section 313, and its distal end then tapers into a minor flow portion 312 of central passage 302. Distal of the point where minor flow portion 312 of central passage 302 begins, slots 315a and 315b are defined and extend transversely into the plates relative to the direction between the inlet and the outlet of central passage 302 and extend laterally across separation plate 300 between the sides of the passage. Major flow outlet ports 314a and 314b can be used for connecting to a major flow manifold (not shown) that receives the major flow of fluid in which the minor portion of the particulates greater than the cut size is entrained.

As will be apparent from the preceding description, a number of gentler steps are used in the central passage of separation plate 300 than in the preceding embodiments of FIGS. 5A and 5B, and 6A and 6B, to improve the efficiency of separating larger particulates (i.e., approximately $5\mu$ to $10\mu$ in size); larger particulates tend to have greater wall losses due to impaction on the "steps" of the telescoping profile. The gentler steps will not focus the small particulates as well as in the other embodiments, however, so the outward expansion provided by diverging section 313, followed by a final steep step into minor flow passage 312 to focus the small particulates seems to improve the efficiency of the separation (at least in simulations). The flow of larger particulates does not expand out much in diverging section 313, and is thus less likely to impact on the final step into minor flow passage 312.

In all other respects, separation plate 300 operates like separation plate 100, and can be modified to collect the major flow like separation plate 200. It will also be apparent that a plurality of separation plates 300 can be stacked, just as in the previous embodiments, to increase the volume of fluid processed.

Particulate Collection

Once the particulate concentration of the fluid stream has been enhanced by the use of a virtual impactor as described above, collection of the concentrated particulates can be effected. It should be noted that impact based collectors (as opposed to the virtual impact collectors described above) can also achieve significant particulate concentrations. However, the impact surface portion of such impact collectors is generally an integral portion of the impact collector, and it is not practical to archive the impact collector itself. The collection surface of impact collectors is generally rinsed with a fluid to obtain the collected particulates for analysis. While such particulates collected in that fashion could also be archived, the volume of fluid required to rinse the collected particulates from the impact collector significantly increases the volume of material that must be archived. Furthermore, the steps of rinsing, collecting, and storing the rinsate add significant time and effort (and thus cost) to archiving particulates. The use of a virtual impactor enables an archival surface to be employed that is a separate component. Such a separate component can be readily removed from the virtual impactor and replaced with a fresh surface for collecting particulate samples. The archival surface on which the sample have been collected can then be stored without significant additional processing until needed.

Any surface material amenable to spot deposition can be used. The present invention contemplates several different deposition methods. A first method involves directing the minor flow described above toward a filter through which the fluid in the minor flow can pass and upon which the particulates are deposited. In a different embodiment, the particulates are directed toward an impaction surface that is enveloped in a vacuum system. The archival (impaction) surface can also be coated with a material that aids in the deposition and retention of particulates that have impacted on the surface.

FIG. 8 schematically illustrates an archival collection system 330 that uses a porous hydrophilic filter medium 336 as the deposition surface. Preferably a hydrophobic material 338 would be deposited on top of porous hydrophilic filter medium 336. Openings 342 in hydrophobic material 338 direct particulates 334 entrained in a minor flow 332 toward locations on porous hydrophilic filter medium 336 that particulates will be collected upon. The fluid in which the particulates are entrained passes through the porous hydrophilic filter medium 336, leaving the particulates deposited on the surface. A vacuum source 340 can be beneficially employed to ensure that the minor flow fluid passes through the porous filter, rather than being diverted around sides of the porous filter.

Preferably the area between the introduction of the minor flow and the filter is sealed, so the particulates will not be lost prior to impact. The sealing preferably extends between the bottom of the porous filter and vacuum source 340. While not readily apparent from FIG. 8, it should be understood that porous hydrophilic filter medium 336 moves relative to the position of the minor flow, so that particulates collected from the minor flow at different times are associated with different (and known) locations on the porous filter. In general, it is anticipated that it will be simpler to move the archival surface than the virtual impactor, although movement of either the virtual impactor or the archival surface will enable particulates to be deposited on specific spaced-apart portions of the archival surface as a function of time. Regardless of which component is moved, preferably any sealing system employed should be capable of accommodating the required movement.

As shown in FIGS. 8 and 9, the minor flow is directed towards the archival surface as three separate streams. It should be understood that either few or more than three minor flow streams could alternatively be employed as well. The benefit of employing multiple minor flows is that, as described above, individual virtual impactors can be fabricated to selectively direct particulates of a desired size into the minor flow. Thus, by employing a plurality of virtual impactors, each concentrating a different particulate size into their respective minor flows, particulates of different sizes can be directed onto different locations of an archival surface. Alternately, particulates of the same size can be deposited in different locations, permitting duplication of sampling to occur, to facilitate multiple testing, perhaps at different times.

FIG. 9 schematically illustrates an archival collection system 350 that uses a non-porous archival surface 346 as the deposition surface. In archival collection system 350, the particulate-laden fluid is accelerated through a minor flow outlet nozzle of a virtual impactor to impact the surface. Preventing particulates from bouncing off of non-porous archival surface 346 is a key aspect of this approach.

Note that in both FIGS. 8 and 9, a surface coating or layer has been applied on top of the archival surface to define receptacles for spots. Such a coating (hydrophobic material 338) is not required, but is a useful addition. Regardless of whether a porous or non-porous archival surface is employed, several different surface treatments may be useful in increasing the efficiency of spot formation. For example, a common problem with surface impaction is that particles bounce off the surface, return to the fluid stream, and are swept away. It is preferable to coat the surface to promote particle adhesion. Such surface coatings include, but are not limited to, charged chemical species, proteins, and viscous substances that increase the impact force required to enable the particulates to bounce away from the archival surface. Details of exemplary coatings that can be beneficially employed in the present invention are described below. It should be noted that a person skilled in the art will recognize that many other coatings, having other physical and chemical properties, can be beneficially employed to aid in the collection of specific types of particulates. In at least one embodiment, the coating is on the order of 100 microns thick, while the archival surface itself is in the order of 100 millimeters thick.

It should be noted that the archival surface, with or without a coating, need not be flat. Preferentially, a surface with portions raised significantly above the bulk of the surface can also be used to collect spots of particulates. For example, a textured surface with portions raised substantially above a background portion of the surface can be used to collect spots of particulates. Such textured surfaces are disclosed in commonly assigned U.S. Pat. No. 6,110,247, the disclosure and drawings of which are hereby specifically incorporated herein by reference. Such surfaces reduce the tendency of particles to bounce and therefore increase spot formation efficiency.

Archival Surface Coatings

FIGS. 10 and 11 schematically illustrate how coating an impact collection surface, such as an archival surface, with a material can substantially enhance the efficiency of that surface. FIG. 10 shows a fluid 410 in which particulates 414 are entrained, moving relative to a (prior art) impact collection surface 412 that is not coated. Particulates 414 are separated from the fluid by striking against impact collection surface 412. FIG. 11 shows fluid 410 moving toward a coated impact collection surface 416, which has been coated with a material that retains substantially more of the particulates entrained in fluid 410 than would an uncoated surface. By comparing FIGS. 10 and 11, it will be apparent that substantially more particulates 414 are collected on coated impact collection surface 416 than on impact collection surface 412.

The relatively greater density of particulates 414 evident on coated impact collection surface 416, compared to impact collection surface 412, is due to a characteristic of the coating that causes it to better retain particulates and thus more efficiently separate the particulates from the fluid in which they are entrained, compared to the prior art impact collection surface that is not coated. In the embodiment of the present invention shown in FIG. 11, the geometry of impact collection surface 416 is generally irrelevant. The coating of the present invention can be applied to the impact collection surfaces in almost any impact collector or virtual impact collector. Simply by coating surfaces on which a stream of particles impacts with one of the materials described below, a substantial increase in the efficiency with which the particulates are separated from a fluid and collected is achieved.

Figure 12:
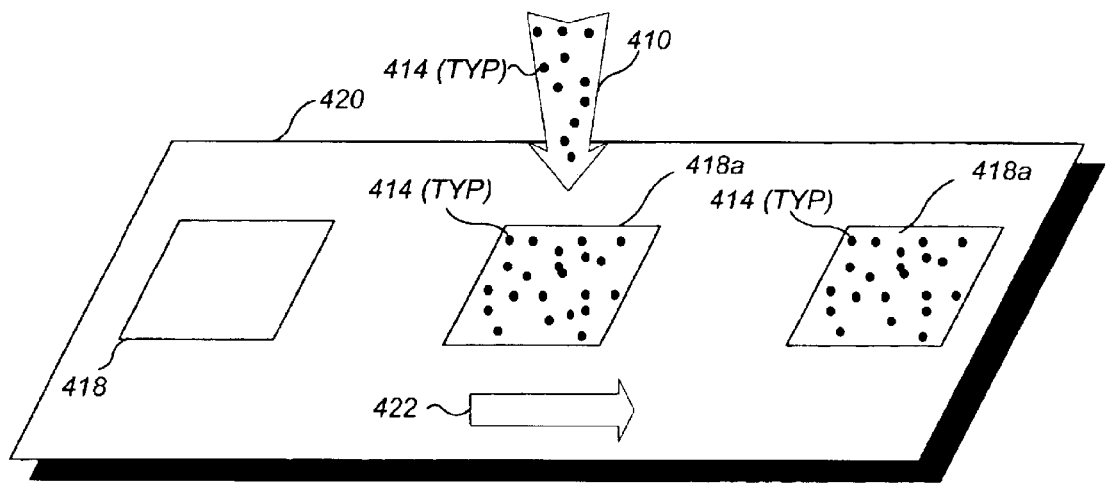

FIG. 12 schematically illustrates an embodiment of the present invention in which a plurality of coated areas 418 are applied to an upper exposed surface of an elongate tape 420. As illustrated in this Figure, tape 420 is advanced from left to right, i.e., in the direction indicated by an arrow 422. Tape 420 thus moves past a stream 421 of fluid 410 in which particulates 414 are entrained. Stream 421 is directed toward the upper surface of the tape. As the tape advances, fresh coated areas 418 are exposed to impact by particulates 414. The particulates that impact on these coated areas are at least initially retained thereon, as shown in coated areas 418a. In the embodiment illustrated in FIG. 12, coated areas 418 and 418a are not contiguous, but instead are discrete patches disposed in spaced-apart array along the longitudinal axis of tape 420. Various types of material described below can be used to produce coated areas 418.

Figure 13:
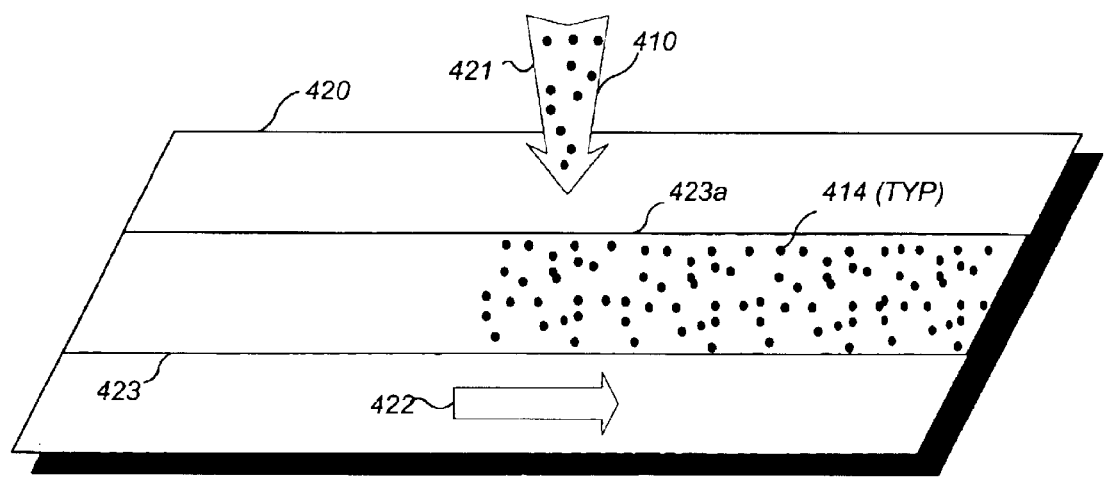

In an alternative embodiment shown in FIG. 13, a continuous coated impact collection surface 423 extends longitudinally along the center of a tape 420'. As tape 420' advances in the direction indicated by arrow 422, stream 421 of fluid 410 with entrained particulates 414 is directed toward the upper surface of the tape. Particulates 414 are retained by the coating, as shown in a coated impact collection surface 423a. As tape 420' advances in direction 422, coated impact collection surface 423 is exposed to impact by particulates 414 carried in stream 421. In the embodiment that is illustrated, the coating does not cover the entire upper surface of tape 420'. However, it should be understood that any portion or the entire upper surface of tape 420' can be covered with the coating.

The material used for producing coated impact collection surface 423 and other coated areas or surfaces employed in this description for collecting particulates in accord with the present invention is selected because of certain characteristics of the material that increase the efficiency with which the particulates are separated from the fluid in which they are entrained. Each material used for a coating has certain advantages that may make it preferable compared to other materials for separating a specific type of particulate from a specific type of fluid. For example, for use in collecting particulates in a dry air or other dry fluid, a material called TETRAGLYME can be used to for the coating. This material is hydrophilic until it is exposed to water and when dry, is relatively very sticky, tending to readily retain particulates that impact it. However, once water is sprayed onto the TETRAGLYME coated surface so that it is wetted, the coating becomes hydrophobic. When hydrophobic, the TETRAGLYME coated surface is no longer sticky or tacky, and in fact, readily releases the particulates that previously were retained by it. The water (or other liquid containing water) easily washes the particulates away from the coated impact collection surface. TETRAGLYME, which is available from chemical supply houses, is bis(2-[methoxyethoxy] ethyl) ether tetraethylene glycol dimethyl ether dimethoxy tetraethylene glycol and has the formula: $CH_3OCH_2(CH_2OCH_2)_3CH_2OCH_3CH_3$—O—$CH_2$—$CH_2$—O—$CH_2$—$CH_2$—O—$CH_2$—$CH_2$—O—$CH_3$. Tests have shown that TETRAGLYME coating can collect more than three times as many particulates as an uncoated surface. Water molecules are retained by the molecule by links to the oxygen atoms, as shown below.

$$O:H_2O:O$$

A second type of material usable for a coated particulate collection surface is PARYLENE, which is a tetrafluoromore manufactured and sold by DuPont Chemical Company under the trademark INSUL-COTE™, Type N. The PARYLENE material is characterized by a relatively low coefficient of friction, causing it to be extremely slippery and not sticky. Accordingly, particulates impacting against a coated surface comprising PARYLENE are initially separated from the fluid in which they are carried by the impact with the coated surface and are initially retained by the coated surface. However, these particulates are readily washed away from the PARYLENE coated surface by water or other liquid sprayed onto the coating. The particulates retained by a PARYLENE coated surface on tape 420' are readily washed away from the coating by water or other liquid spray.

The TETRAGLYME material is an example of a class of materials that has two distinct states related to particulate collection. When dry and hydrophilic, the TETRAGLYME material is in a first state, in which it is sticky and is very efficient at separating particulates from the fluid in which they are entrained, compared to an uncoated surface. However, when wetted, the TETRAGLYME material changes to its second state, in which it readily releases the particulates.

Figure 14:
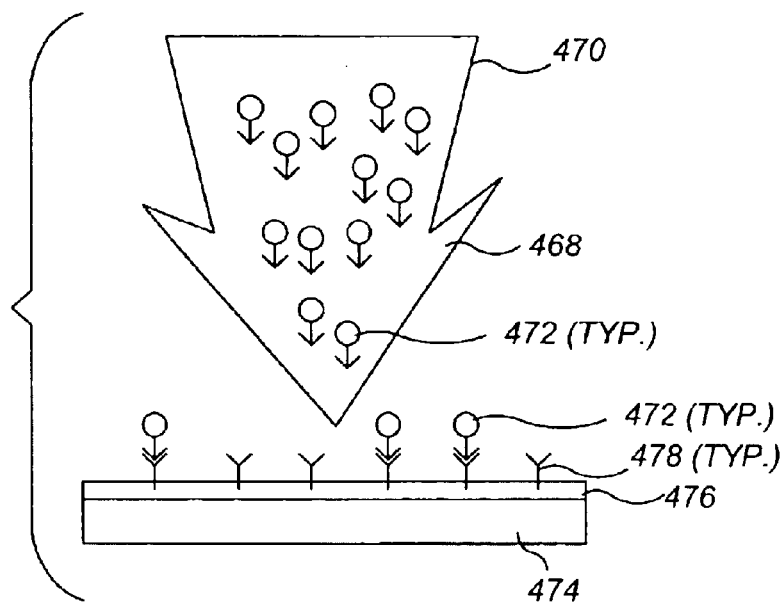

As shown in FIG. 14, a mono-layer material 476 can be applied to a surface 474 of a particulate collector to separate specific biological particulates 472 from a fluid 468 such as air or a liquid in which they are entrained. It is contemplated that the fluid conveying the biological particulates may also include blood. A stream 470 of the biological particulates is directed at material 476, so that the biological particulates impact thereon. Mono-layer material 476 comprises a plurality of antibodies 478 that are selected to link with the antigens on biological particulates 472. For example, if biological particulates 472 comprise anthrax spores, and antibodies 478 are selected that are specific to anthrax spores, the anthrax spores will be readily separated and retained by linking with the antibodies on the coating. These anthrax spores may then be identified based upon an appropriate analysis. The type of analysis employed is outside the scope of this disclosure. Those of ordinary skill in the art will recognize that based on the nature of the targeted particulates, a specific analytical procedure may be more or less appropriate.

Figure 15A:
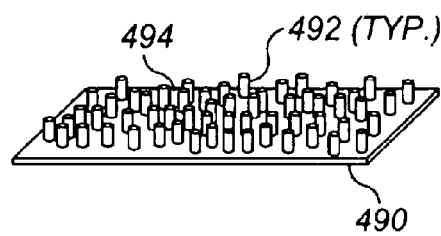
Figure 15B:
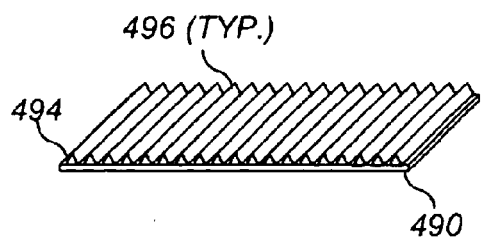

It is also contemplated that the coated impact collection surface need not be planar. Indeed, it is likely that enhanced particulate collection efficiency can be achieved by using a non-planar coated surface to collect particulates. FIG. 15A illustrates an enlarged view of a portion of one preferred embodiment for a textured particulate collection surface 490 having a plurality of outwardly projecting rods 492 distributed thereon. The outwardly projecting rods increase the surface area of particulate collection surface 490, which is provided with a coating 494 of one of the coating materials discussed above, and also increase the "roughness" of the surface to further enhance the collection efficiency of the coating. Coating 494 may be applied over rods 492 or applied before the rods are attached. Alternatively, other projecting structures such as ribs 496 may be employed on textured particulate collection surface 490, as shown in FIG. 15B.

In at least one embodiment, the archival surface incorporates a material that helps maintain the particulates deposited on the archival surface in good condition, without substantial degradation. For some particles, such as living cells, this material may be a liquid that contains nutrients. Applying a hydrogel or equivalent coating on the archival surface would allow localization of water. The water can be used to deliver salts, sugars, proteins, and other nutrients to enable the cells to survive on the archival surface during the time interval between deposition on the archival surface and subsequent analysis of the collected samples of particulates.

For all of the above surfaces, some portion of the analysis/detection scheme could be included as part of the surface. For example, if the analysis employed to detect a specific particulate involves incubating the collected particulates (some of which are likely to be bioparticles) with a reagent, the reagent can be incorporated onto the surface so that the incubation period is initiated upon deposition.

Orientation of Archival Surface Relative to Virtual Impactor

As noted above, because the location of a "spot" of particulates deposited on the archival surface is indicative of a time the particulates were collected, it is preferable to move the archival surface relative to the virtual impactor, at least at spaced-apart times to form spots of particulates (or continually to form streaks of particulates). Moving the archival surface at successive time intervals permits multiple sample spots to be deposited on a single archival surface without commingling the spots. The time at which each spot is deposited is associated with the spot. Alternatively, time can be linear in its association with a position in a streak of particles that are deposited continuously.

Figure 16:
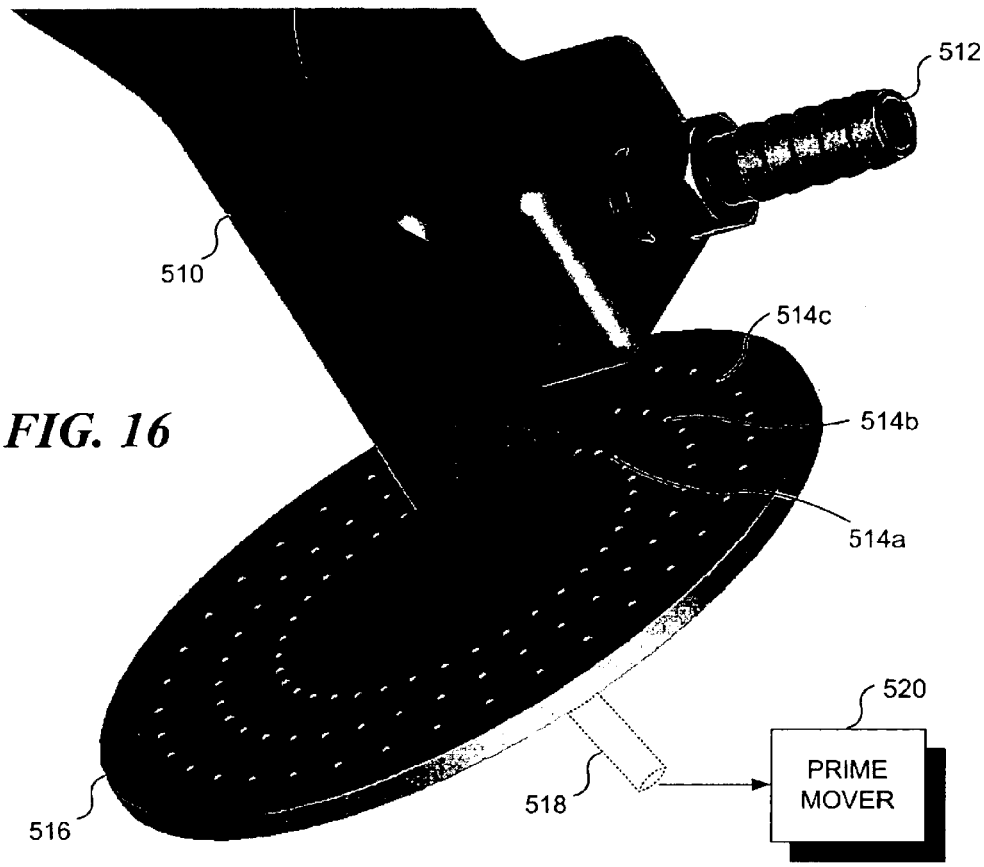

One embodiment providing for intermittent relative motion between the archival surface and the adjacent stream of particulates is shown in FIG. 16, in which a virtual impactor 510 is fixedly mounted over a movable archival surface that is formed in the shape of a disk 516. The minor flow of particulates is S directed at the disk. A major flow 512 containing particulates of non target size exits virtual impactor 510 orthogonally with respect to the minor flow, to prevent particulates entrained in the major flow from being deposited on disk 516. While not shown, it should be understood that disk 516 could be further separated from major flow 512 by a protective housing.

The nozzles directing the minor flow toward disk 516 cannot be seen in FIG. 16, but virtual impactor 510 includes three minor flow outlets, all of which are oriented to direct particulates towards spot deposition areas 514a–514c. As disk 516 rotates beneath virtual impactor 510, the minor flow nozzles of virtual impactor 510 direct particulates to a new deposition area. Note that disk 516 shows three concentric rings of spaced-apart spots in three different annular deposition areas, area 514a defining the inner ring of spots, area 514b defining a middle ring of spots, and areas 514c defining an outer ring of spots. Disk 516 is preferably indexed (not shown) so that the spots are defined at discrete predetermined positions around the deposition areas, that enable the position of each spot to be associated with a specific time, and enable the particulates to be accurately directed toward the disposition of each spot on the disk. It should be understood from FIG. 16, and the preceding description, that deposition areas 514a–514c preferably each include a plurality of depressions formed into disk 516, either as openings in a coating on disk 516, or depressions formed into the surface of disk 516, where each spot of particulates is to be deposited. However, while such openings/depressions are anticipated to increase collection efficiency, they are not required.

Disk 516 can be moved using an appropriate prime mover 520, such as a stepping motor. As shown, one such means includes a shaft 518 detachably coupled to disk 516 and driven by prime mover 520. It is anticipated that disk 516 will remain stationary for a desired time interval, and then will be rotated a sufficient amount to align another set of depressions in the deposition areas with the minor flow nozzles of virtual impactor 510, so that the spots of particulates can be deposited within the depressions, if depressions are indeed provided. The virtual impactor can be cycled on and off during the movement if desired.

As noted above, is also possible to deposit streaks of particulates instead of spots. In a more elaborate embodiment, the archival surface is continually moved at a fixed rate, resulting in annular rings defined by streaks of particles on the archival surface, instead of discrete spots. The use of streaks somewhat simplifies the operation of the collector, in that it can operate continuously, rather than being cycled on and off.

Figure 17A:
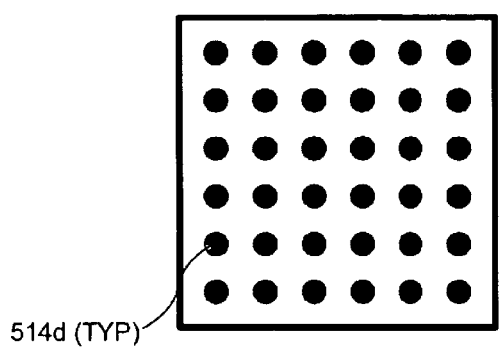
Figure 17B:
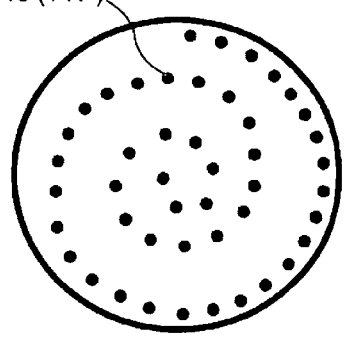

Note that more or fewer minor flow nozzles can be incorporated into a virtual impactor. Preferably, each virtual impactor minor flow nozzle will be directed to a different location on the archival surface. It should also be noted that different configurations of archival surfaces can be employed (i.e., shapes other than disks), and that different configurations of spots can be deposited on archival surfaces (i.e., configurations other than streaks or concentric rings of spots). FIG. 17A shows a quadrilateral shaped archival surface on which deposition areas 514d are oriented in an array extending orthogonally in two directions. FIG. 17B shows a second disk-shaped archival surface, on which deposition areas 514e are oriented in a spiral array. It should be understood that any of deposition array 514a–514e illustrated and discussed above can be one or more of: (1) a depression on the archival surface; (2) an opening in a coating on an archival surface; (3) an aggregate of particulates deposited in a spot; and (4) an area in which an aggregate of particulates are to be deposited without regard to the shape of the deposit.

Exemplary Archival Collection System with Employing Dual Ticket Magazines

One preferred embodiment of an automated system that automatically changes collection surfaces when triggered to do so (or according to a pre-programmed schedule) includes a plurality of tickets. This Indexed Particle Collection System (IPCS) allows multiple samples to be taken without user intervention. Unused collection tickets are stored in a "magazine." When a new sample is needed, the indexed system automatically removes a new collection ticket from the fresh magazine and places it in position for sample collection. When the sample is complete, the collected sample is moved into a spent magazine and a fresh ticket is placed into positioned for collection of the next sample. In a prototype unit up to 24 sample tickets fit in a magazine. Samples can be changed on a pre-programmed time interval or by a trigger signal.

Figure 18A:
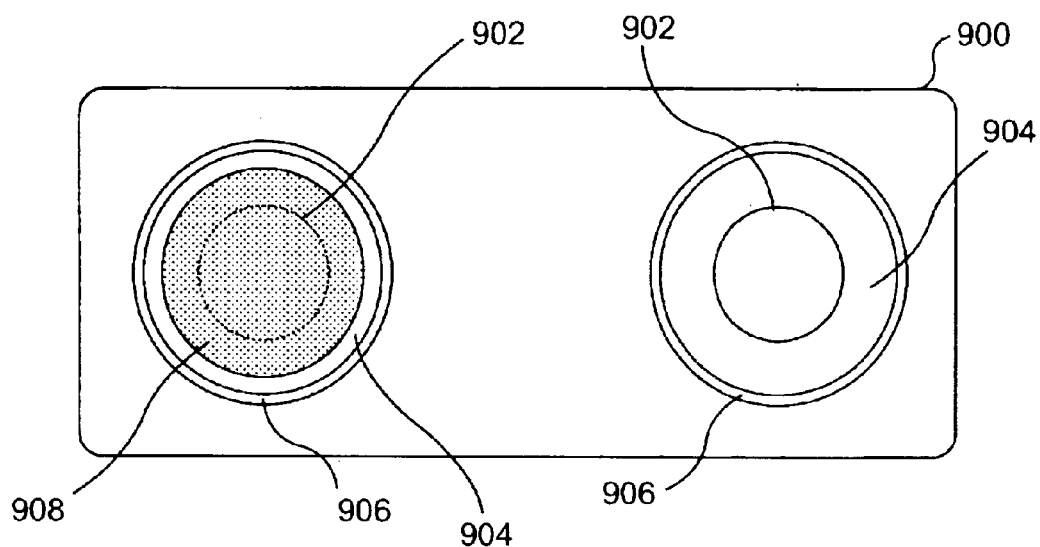
FIG. 18B is a bottom view of the ticket of FIG. 18A.
FIG. 18C is a side view of the ticket of FIGS. 18A–B, illustrating a punch being used to remove a disposable collection surface.
FIG. 18D is a block diagram of the components of an exemplary particle collection system utilizing the ticket of FIGS. 18A–C.
FIG. 18E is a block diagram of the components of an exemplary archival spot collection system.
Figure 18B:
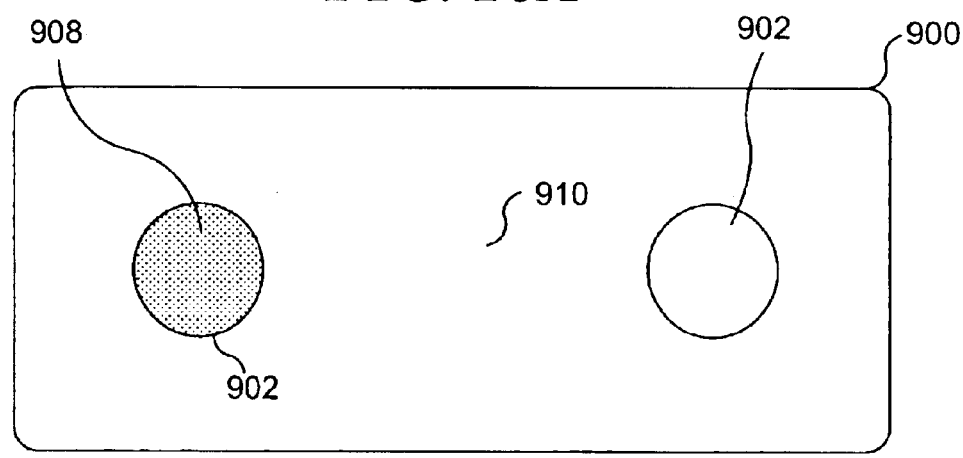
Figure 18C:
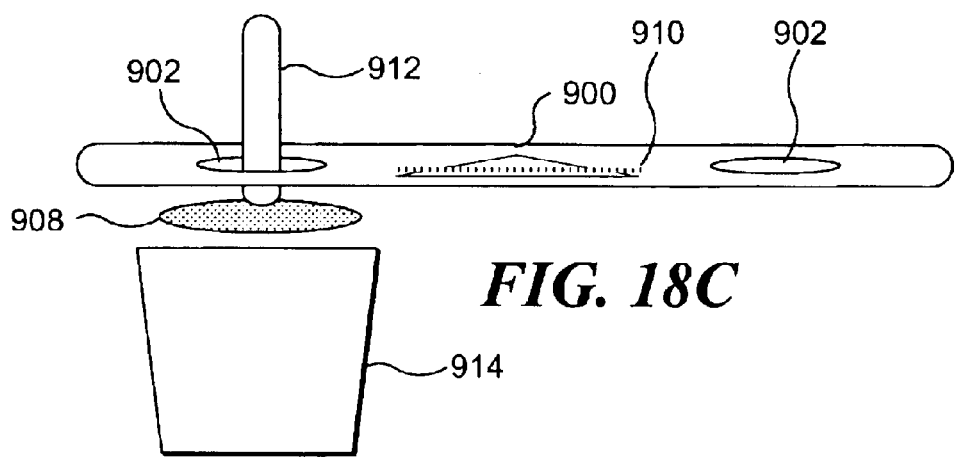

FIG. 18A shows a plan view of an exemplary ticket 900, which preferably includes two collection areas, defined by raised lips 906. In a prototype unit, ticket 900 was fabricated from metal, although other durable materials, such as polymers, can be employed. If tickets are to be reused, they should be fabricated from a material that is easy to sterilize, to avoid cross contamination. Inside each lip 906 is a generally flat surface 904. Generally in the center of each flat surface 904 is an opening 902. A disposable impact surface 908 is placed inside each raised lip 906. In FIGS. 18A–18C, only one impact surface 908 is shown, however, it should be understood that preferably each ticket includes two impact surfaces. While both impact surfaces can be analyzed, it is anticipated that a useful sampling protocol will call for one impact surface to undergo analysis and one impact surface to be archived. As has been generally discussed above, each impact surface is disposed in fluid communication with a minor flow path from a virtual impact collector. As each ticket includes two collection areas, ticket 900 is designed to be employed in a system whose virtual impactor provides two minor flows, spaced apart so that each minor flow is generally directed toward flat surfaces 904, upon which an impact surface will be placed. Also as discussed above, the minor flow is preferably configured to deposit small spots of particles on the impact surfaces.

FIG. 18B is a bottom view of exemplary ticket 900, again showing only a single impact surface 908. Lips 906 are not present on the bottom of the ticket. A logo 910 is included, to provide a reference to ensure that tickets are loaded in the proper orientation. FIG. 18C is a side view of exemplary ticket 900, again showing only a single impact surface 908. One or both of the impact surfaces are removed from the ticket and placed in a sample container 914. A punch 912 or rod can be employed to facilitate the removal of impact surface 908 from ticket 900. Note openings 902 provide access to push the collection surface out of the ticket into the vial to recover the sample. The ticket design gives two parallel samples that can be removed separately, allowing one to be analyzed and one kept in reserve, or allowing parallel analysis to be done.

Figure 18D:
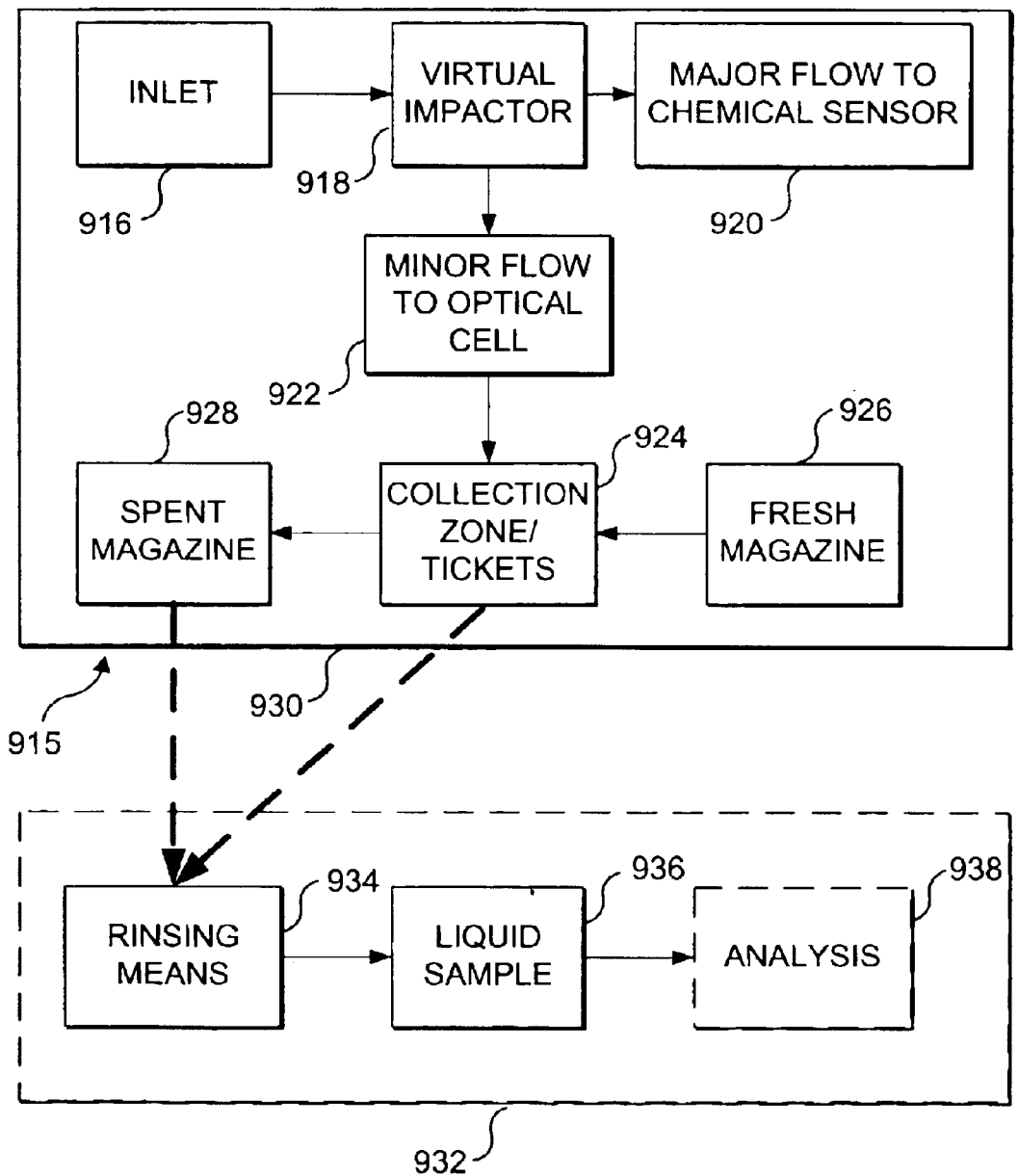

FIG. 18D illustrates a prototype system for using tickets 900. System 915 includes a fluid inlet 916 that diverts a portion of a flow of fluid into system 915. Not separately shown is a fan, which is preferably included to force fluid through system 915. As generally described above, the virtual impactors used in the present invention separate a flow of fluid into minor and major flows. A virtual impactor 918 separates the fluid into a major flow 920 that is preferably directed to a chemical sensor, and a minor flow 922 that preferably passes through an optical cell. The optical cell in the prototype employed a laser based particle counter, that triggered sample collection when the level of particles in the minor flow reached a predefined threshold. It should be understood that other parameters, such as elapsed time, could also be used to trigger a sample collection.

To collect a sample, a ticket is loaded into a collection zone 924 from a fresh magazine 926. Once the sample is collected, the ticked is moved to a spent magazine 928, and a new ticket is placed into the collection zone from fresh magazine 924. While not separately shown, it should be understood that a prime mover is employed to move the tickets from the fresh magazine to the collection zone, and then to the spent magazine. Each impact surface 908 of the tickets can incorporate any of the coatings discussed above, or no coating. Preferably each impact surface on a ticket is provided with the same coating, particularly if one impact surface will be archived. Of course, in some collections strategies, such as comparing one coating to another, different coating can be employed. Note that system 915 does not incorporate any rinsing of the sample to produce a liquid sample, but rather is intended for use in applications where the samples would be returned to a laboratory for analysis.

General Rinse System Concept

While system 915 and is quite useful for collecting dry samples for later analysis or archiving, many analytical techniques require samples in liquid forms. It would be desirable for a sample collection system to provide a liquid sample, not only to eliminate the requirement of generating such a liquid sample at the laboratory, but most importantly if analytical instrumentation requiring liquid samples is integrated into the collection system. One way to include such functionality would be to provide a rinsing module as a separate, add on module to a sampling system, as is indicated by module 932 in FIG. 18D. Such a module could interface with system 915 in a minimal way, such that when a liquid sample is required, the corresponding ticket is transferred from the either the collection zone or the spent magazine to a rinse means 934 in the rinse module. Such rinse means are described in more detail below. Such a modular system enables design improvements to be made incrementally to either the collection system or the rinse system, without affecting the other module. Another option would be to integrate the sample collection and rinsing into a single unit. Rinse means 934 will produce a liquid sample 936, which can then be taken to a laboratory, or more preferably, be analyzed in an onboard analytical unit 938.

The basic steps of the rinsing preferably include: 1) receiving a signal to rinse a collected sample; 2) removing the appropriate ticket from either the collection zone or the spent magazine; 3) delivering the appropriate ticket to the rinse module; 4) applying a rinse liquid to the ticket; 5) agitating or otherwise performing steps to facilitate removal of material from the ticket; 6) delivering the liquid sample to a sample vial; and 7) delivering the required liquid sample volume from the sample vial to the analysis system.

One variation would be to include the step of removing only the portion of the collection surface on the ticket that contains the spot of impacted particles. This will minimize the rinse volume required to remove the particles. Such minimal removal may correspond to a physical removal (or "punching out") of the impaction spot. Conversely, such minimal removal can be achieved using means (such as a sample tube that is brought in contact with, or immediately adjacent to, the surface of the ticket) that isolates the spot and minimizes the rinse area to be rinsed.

It is anticipated that a target rinse volume would result in the collection of 1 millimeter or less of fluid sample. It is also anticipated that not all samples collected in the field will need to be rinsed in the field. The rinsing will preferably be performed based on a predefined trigger event, an external input, or based on some predefined schedule. Most often, such a trigger event will cause the system to collect a liquid sample from the ticket in the collection zone. However, it would be useful to include the ability to collect a liquid sample from a previously used ticket stored in the spent magazine. Such an ability would be useful, but not required. Arrows in FIG. 18D indicate the ticket is obtained from either the collection zone or the spent magazine.

There are a number of technological features and techniques that can be utilized to improve both the efficiency of the particle impaction process as well as the efficiency of particle removal after impaction. These features include:

Use of a porous impaction surface: in traditional impactors, the surface is solid, causing the air directed towards the surface to diverge tangentially. The air retains some portion of particles, meaning that this fraction fails to impact on the surface. If the impactor surface contains very small pores, some or all of the airflow passes directly through the surface, retaining those particles that would otherwise be lost in a traditional impactor. To be effective, the pores must either be smaller than the desired particle size, or the material must contain some other means for capturing the particles as the pass by (such as an electrostatic charge).

Use of a dissolvable impaction surface: after particles are impacted, their collection can be assisted by use of a dissolvable impaction surface. Ideally, the surface is comprised of a substance that is tolerable in the resultant liquid sample, or can be easily removed from the liquid sample. An example of a tolerable substance is cellulose, which can be formed into an impaction surface and then dissolved by exposure to the enzyme cellulase. Whether any particular substance is tolerable or easily removable depends on the specific particles of interest, as well as intended methods of analysis. The surface structures illustrated in FIGS. 15A and 15B could be formed out of a soluble material. Such an impact collection surface could be fabricated into a long strip, which is moved into place for collection, then moved to the next position for rinsing (by dissolving the structures or a coating on the structures). Chitosan (which breaks down in the presence of a specific solution) and aerogels are examples of such materials, as well as the materials discussed in greater detail above.

Dissolution of surface by other methods: it is also possible to use surfaces or surface layers that lose structural integrity when exposed to other conditions, such as ultraviolet light (e.g. depolymerization), heat, acoustics, magnetic fields, electric fields, or other phenomena. For example, a collection surface could be charged to include an electrostatic field, thereby collecting particles having an opposing charge. Reversing the polarity of the applied field would repel the collected particles. Polonium or other materials can be used to apply a charge to the particles before they, impact the collection surface to facilitate such electrostatic collection/repulsion. Depending on the ambient temperatures where the system is to be used, the collection surface could be a frozen or semi-frozen impaction surface that is melted to obtain the sample. Similarly, a material having a relatively low melting point could be used either as the entire impact surface, or a coating on the impact surface. Upon the application of heat, the surface or coating would melt and flow into a sample vial, along with the sample. Such a material must be either readily removable from the sample, or must not interfere with the analysis to be employed. Filters or absorbents can be used to remove some types of unwanted material.

Use of a removable surface coating: the particles may also be efficiently rinsed if a layer on top of the surface is removable. The simplest such example is a dissolvable coating, such as a sugar layer. Another possibility is a surface coating that is held initially by a chemical bond that is later broken. One such example is a layer of streptavidin that is chemically bonded to a layer of biotin, which is covalently attached to the surface. If the rinse fluid contains excess biotin, the streptavidin will release from the surface. Many other such scenarios are possible. A viscous coating can be used, which when heated or cut with a thinner flows easily, enabling the coating to be poured into a sample container.

Continuous surface rinse: use of a continuous process that immediately removes impacted particles. One example is a liquid jet directed at the impaction region. A different example involves use of a continuous layer of water run across the impaction surface. In another embodiment, the surface itself can be rotated or translated such that newly-impacted particles become wetted and rinsed, perhaps with the aid of ultrasonics, vibration, or dissolving coatings. A number of other scenarios are possible. One preferred waterfall approach involves continually pumping fluid over a surface toward which a fluid jet is directed. In such continually rinsing embodiments, the rinse fluid can be continuously collected and re-circulated.

Use of an impaction surface with protrusions or roughness: use of surface roughness, such as impaction microstructures, will enhance the collection efficiency of particle impaction by providing an additional filtering effect. In addition, the surface features may be removable or dissolvable in order to aid in particle recovery. As noted above, FIGS. 15A and 15B are exemplary of such microstructures.

Use of a live impaction surface: use of a surface that can be deformed, flexed, twisted or vibrated to facilitate the removal of a sample. This can be done either in conjunction with a rinse fluid, or in the absence of a rinse fluid. One variation on such a live impaction surface involves a "balloon" type impaction surface, which is inflated such that the surface area of the balloon increases for sample collection, and then decreases as the balloon is deflated for rinsing. Note the deflated balloon has a smaller surface area, so that less fluid is required for rinsing, and the bond between the impacted particles and the balloon's surface is disturbed, requiring less force to remove the particles. An inflated balloon could be coated with a material that tends to flake off when the balloon is deflated. Such a material coating would preferably be relatively inflexible, such that the change in the balloon's size caused the coating to fracture. Sugar based coatings, and other materials that tend to form crystalline lattice structures (such as salts) are useful in such an application.

Use of extended collection times: the time the impact surface is exposed to the minor flow can be extended, thereby accumulating larger spots that would tend to agglomerate into particles, making them larger and stickier, and thus easier to collect.

Soaking or dipping the collection surface: use of a bath of rinse fluid that the collection surface, or a portion thereof, is repeatedly dipped into, or placed into for an extended period. This could be particularly useful if the collection surface includes a plurality of structures. Consider a plurality of elongate, "flagellating" strips whipping around in the minor flow to collect sample, which are then dissolved into or rinsed off by placing them into a fluid bath (like rinsing a mop).

Incorporating analytical reagents into collection surface: use of a test strip as the collection surface. Such test strips generally include one or more reagents, which must be exposed to a "developing" solution to complete the analysis. Instead of rinsing such a collection surface to obtain a sample, the collection surface is exposed to the developer, and the collection surface itself provides an indication (generally a color change) as to whether a suspected particulate is present.

Use of an inert rinse fluid: preferably the rinse fluid will be inert, unless a specific rinse fluid is required to dissolve a coating, or required for some other functionality described above. Jets of fluid can be used to remove the impacted particles.

Manipulate the orientation of the collection surface to the minor flow: in general, the collection surface (i.e. the impact surface) will be disposed substantially normal (i.e. perpendicular) to the direction of the minor flow. Orienting the minor flow to be parallel to a collection surface would result in the particles entrained in the minor flow settling out onto the collection surface as a function of the mass of the particles. Such a surface could be periodically rinsed, and sub portions of the surface relating to specific particle masses, or a range of particle masses, could be individually rinsed.

Use of a wiper blade: either in conjunction with the use of a rinse fluid, or alone, a blade can be used to remove collected particulates. A "windshield wiper" approach corresponds to the use of a liquid sprayed onto the collection surface and a physical blade being used to wipe off the particles.

Use of a large volume rinse: a large volume of rinse fluid can be used to remove the particles, and collected into a sample container. The large volume of fluid can be subsequently reduced (such as by evaporation), or the sample container can include binding targets, to which specific particles will bind to (such as the antibody/antigen binding discussed in conjunction with FIG. 14).

Incorporation of colormetric detection: Colormetric detection can be incorporated into many of the above scenarios, such that the presence of a target particle will be indicated by a color change. While such color changes are primarily qualitative, they provide a rapidly recognizable means to indicate which fluid samples include some level of target particles.

Combination of a movable collection surface (or minor flow nozzle) and a fluid rinse or bath: The nozzle of the minor flow could impact onto a disk shaped impact collection surface, which would slowly rotate so that the impact collection surface is dunked into a bath where soaking, vibration, dissolvable coatings or an individual one of, or a combination of the above disclosed techniques is employed to procure a liquid sample. This could be implemented as a continually rotating/rinsing embodiment or as a batch rinse approach. Instead of a disk, a strip of material could be used with a "reel to reel" type configuration where the strip is fed into a collection area, then through a rinse chamber, and then onto a "take up reel".

Note it is contemplated that some embodiments of rinsing systems will beneficially incorporate combinations of the various methods discussed above. Having now discussed rinsing in general, specific examples will be provided, along with other sample retrieval techniques (i.e. non-liquid based retrieval).

Figure 18E:
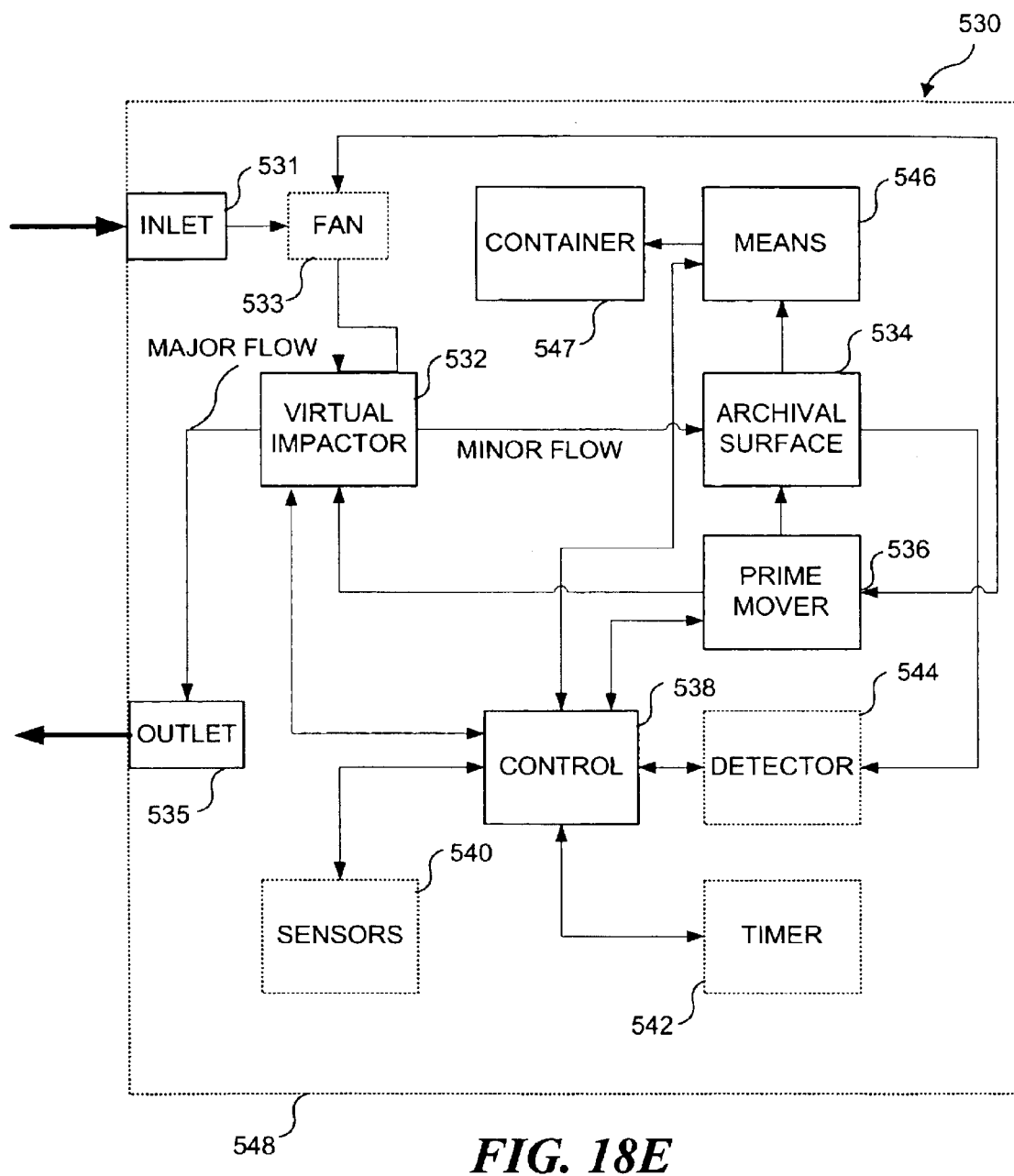
Figure 19:
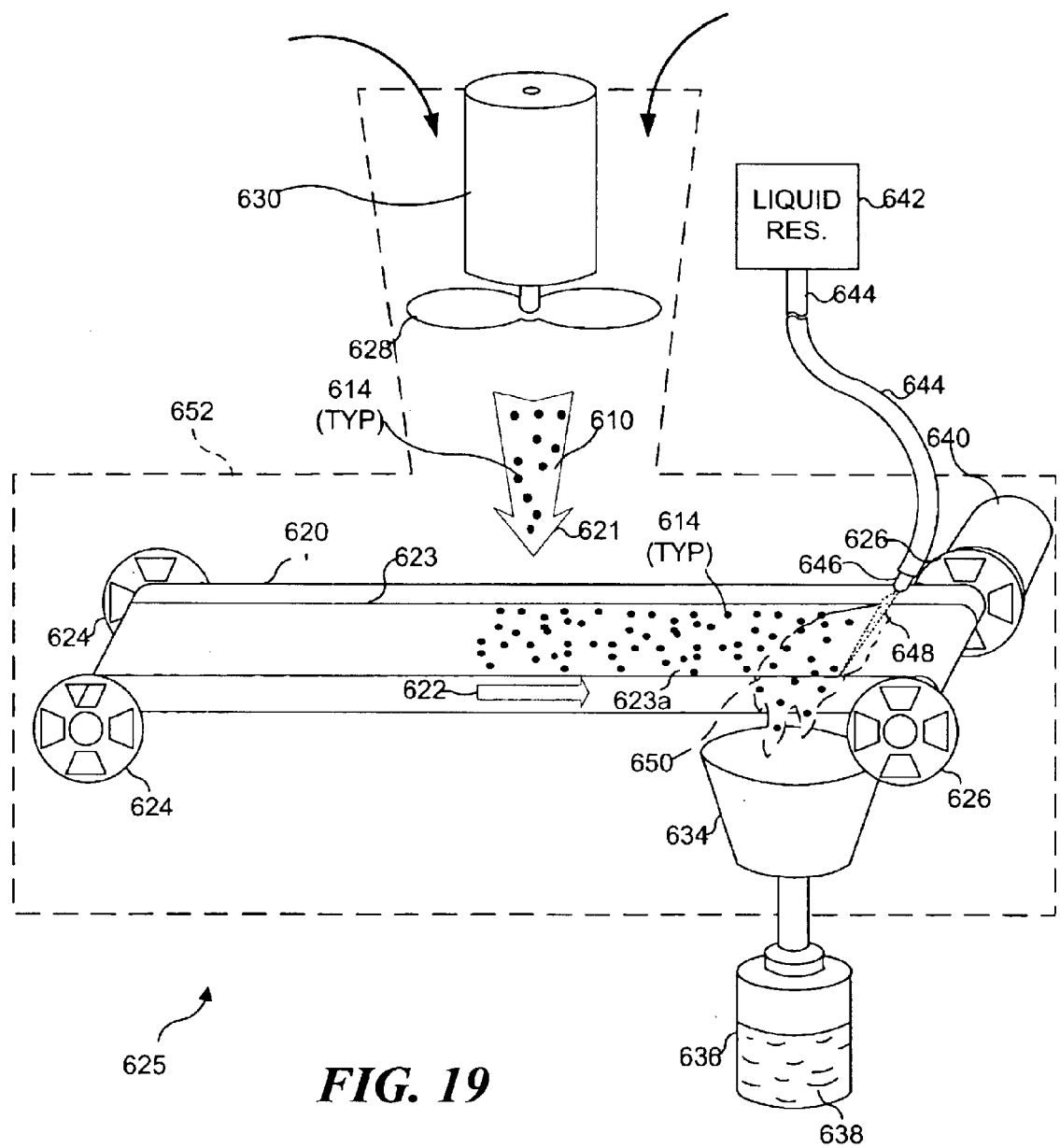
FIG. 19 is a schematic view of an integrated system using a liquid rinse to collect a sample of particles from a collection surface.

Exemplary Archival Collection System with Means for Removing and Transferring Particulates from a Collection Surface to a Container FIG. 18E illustrates an exemplary archival system 530, for collecting and archiving particulates entrained in a flow of fluid. Such particulates can include chemical and biological compounds. System 530 includes a fluid inlet 531 that diverts a portion of a flow of fluid into system 530. A fan 533, which can be centrifugal fan or an axial fan driven by a motor or other prime mover, forces fluid through system 530. It should be noted that the virtual impactors used in the present invention to separate a flow of fluid into minor and major flows function best when the fluid passes through the virtual impactor at about a predefined velocity. While a source of some fluid streams may have sufficient velocity to pass through a virtual impactor without requiring a fan to drive them through the virtual impactor, it is contemplated that many applications of system 530 (such as collecting particulates from a smokestack) will require fan 533. While as shown, fan 533 forces a fluid into system 530, those of ordinary skill in the art will recognize that the fan could alternatively be positioned to draw fluid through system 530, so that the major flow through system 530 is drawn through and exhaust 535 and the fluid comprising the minor flow (after the particulates are deposited on the archival surface), exit through another port (not shown).

System 530 also includes a virtual impactor 532 adapted to separate the fluid into a major flow and a minor flow that includes particulates of a desired size range that are directed onto an archival surface 534. Virtual impactor 532 can one of the virtual impactors described above, although it is also contemplated that other designs of virtual impactors might also be used. A fluid is forced into virtual impactor 532 by fan 533, and as described above that fluid is separated into both a major flow and a minor flow. The major flow is directed to exhaust 535, while the minor flow is directed to an archival surface 534.

Archival surface 534 can incorporate any of the coating discussed above, or no coating. The configuration of archival surface 534 can include, but is not limited to, a plate, a disk, or an elongate tape. Preferably, archival surface 534 can be readily removed and replaced with a new archival surface either when the original archival surface is full, or particulates deposited on the archival surface require analysis.

Means 546 is employed to remove particulates collected on surface 534, and to transfer those particulates to a sample container 547. Specific examples of means 546 are described in greater detail below. Means 546 is operatively coupled to a control 538, which is also discussed in greater detail below.

Preferably, archival surface 534 is coupled to a prime mover 536 that moves the archival surface relative to virtual impactor 532 over time, so that particulates collected at different times are deposited on different portions of archival surface 534. It should be noted that prime mover 536 can instead optionally move virtual impactor 532, instead of, or in addition to, moving archival surface 534.

With respect to embodiments in which prime mover 536 is drivingly coupled to archival surface 534, several different types of motion are contemplated. If archival surface 534 is a disk, prime mover 536 will likely be used to rotate the disk. If archival surface 534 is an elongate tape, then prime mover 536 will likely be used to cause one or both of a take-up wheel or a drive wheel (not shown) to be moved, to cause a corresponding movement in the elongate tape. Note that archival surface 534 is a consumable component, which when full, will be replaced with a fresh archival surface.

Prime mover 536 is controllably coupled to a control 538. The purpose of control 536 is to control the movement of prime mover 536 to achieve the desired movement of either virtual impactor 532 or archival surface 534, and to actuate means 546 when a sample of particulates is to be transferred from surface 534 to container 547. Means 546 can be actuated based on the occurrence of a predefined condition (such as a sensor indicating that a triggering event has occurred), based on an affirmative user command, or according to a predefined sampling protocol. For example, an integrated system can be designed to deposit a plurality of spots during a given time period, where some of the spots are to remain on the archival surface, and others of the spots are to be transferred to a sample container.

It is anticipated that control 538 can be one of a computing device, an application specific integrated circuit (ASIC), a hardwired logic circuit, or a simple timing circuit. In at least one embodiment, software is executed to control the operation of the device, and the control includes memory and a microprocessor. This software preferably includes a program that determines the positioning of the archival surface relative to the minor flow. The software may also include a program that controls the schedule for taking environmental samples at predetermined times, thereby producing a spot on the surface at specific spaced-apart times. In addition, the invention may execute logic that modifies the sampling schedule in accordance with algorithms that are responsive to onboard sensors 540. Finally, the software can monitor the particulate collection, generating a log of the actual time when each sample is taken in association with the disposition of the spot deposited on an archival surface at that time. This log facilitates correlating a specific sample (i.e., a specific spot) with a particular moment in time at which the spot was deposited. Control 538 is shown as being controllably coupled to fan 533. According to one sampling protocol, fan 533 will operate continuously. According to another sampling protocol, fan 533 will operate for a pre-defined period of time while a spot is being deposited on the archival surface, and then will be de-energized by the control. It is preferable that the flow of fluid into the system be interrupted between the deposition of samples that deposited as spots, and when the archival surface is being replaced.

Empirical tests of a prototype device, functionally similar to system 530, and employing a polymeric tape as an archival surface, has confirmed the ability of a virtual impactor to deposit spots of particulates on a movable archival surface.

As noted above, in some embodiments, system 530 may beneficially include sensors 540, which communicate with control 538 to cause a sample to be collected in response to an event that is detected by the sensors (i.e., one or more sensors). For example, an archival system may be mounted in a smokestack of a manufacturing facility, to generate an archival record of emissions from the smokestack. Such a system might be equipped with a carbon monoxide monitor, and when levels of carbon monoxide achieve a predetermined level, controller 538 (based on sensor data from sensors 540) can be programmed to initiate a sampling event, to deposit particulates on the archival surface for later analysis in response to the sensor readings. Such sensors can be used to measure relevant environmental factors that include, but are not limited to, pressure, humidity, temperature, particulate count, and presence of a particular target bio-molecule (such as particular cell types, pathogens, and toxins). Based on the detection of a specific environmental factor by such a sensor, or in accord with a sampling protocol programmed into control 538, one or more of the following functions can be executed by control 538:

- generate a record of the environmental conditions at the time of spotting;
- control the operation of any system components whose performance depends on a measured environmental parameters;
- manipulate a programmed sampling protocol based on measured environmental factors;
- actuate means 546 to transfer collected particulates to a sample container; and
- produce an alert signal (for example, by a radio transmission or a hard-wired signal transmission) to notify an operator of an important change in the environmental conditions (as determined by programmed control parameters).

Referring once again to FIG. 18E, a timer 542 is optionally included to provide a timing signal to control 538. Depending on the type of computing device (or logical circuit) employed for control 538, timer 542 may not be required. Many computing devices do not require a separate timer, and in its simplest form, control 538 may itself comprise a timer or timing integrated circuit.

One or more optional detectors 544 can be included, to analyze particulates deposited on the archival surface. It is expected however, that the archival surface will most often be removed from the system before any of the particulates (i.e. spots) are analyzed. By using a separate detector, the cost of system 530 can be reduced, as detectors are often sophisticated and expensive. Furthermore, many detection methods require particulates comprising the spots to be removed from the archival surface before being analyzed. If detector 544 requires the particulates comprising the spots to be removed from the archival surface prior to analysis, a particulate removal system (generally a liquid rinse directed at a specific spot) must also be incorporated. Particulates comprising the spots can also be removed by scraping, and other means.

Preferably system 530 will often be used in a fixed (permanent) location to monitor a specific geographical location over a long period of time. Spent archival surfaces will be removed for storage and or analysis, and new archival surfaces will be inserted in system 530. It is anticipated that system 530 can also be used as a survey instrument that is moved from one location to another, to sample different geographic regions. Such a survey instrument can be used to obtain samples (spots) from many locations within a region on a single archival surface. This feature has utility in determining the source of a particular contaminant and monitoring a number of locations when the spots on the archival surface are subsequently analyzed.

While not specifically shown, it is further contemplated that system 530 can beneficially incorporate the ability to communicate with a control system at a remote location, to send and receive control signals and other data.

In many applications, it will be important that the system be able to sample a large volume of air (≧300 1 pm), but it is also desirable that the sample collected be deposited in a small area (i.e., as spots ~1 mm in diameter). To achieve these goals, it will be important to achieve the separation of particulates from a large air volume and their concentration in a relatively smaller air volume (i.e., the minor flow). In such applications, it is contemplated that two in-line stages of virtual impaction may be preferable. In the first stage, 90% of the inlet fluid is discarded, and the remaining 10% of the fluid (first stage minor flow) contains the desired particles. This first stage minor flow then enters a second virtual impactor stage with 90% of fluid that enters the second stage being exhausted. Therefore, the two stages have the combined effect of concentrating the outlet minor fluid volume to $\frac{1}{100}^{th}$ of the initial inlet flow volume. This relatively small minor flow should then be in the correct range for depositing the concentration of particulates as spots onto a small surface area. Preferably, the spot density on the surface will be as high as possible, without cross-sample contamination occurring, in order to minimize the required area of the archival surface.

Means for Transferring Particles from a Collection Surface to a Container

In several embodiments of the present invention, a fluid is used to remove and transfer the particulates from collection surface to a container. Depending upon the collector employed, the fluid can be a liquid or a gas. FIG. 19 schematically illustrates a particle impact collector 621 that includes tape 620' having coated impact collection surface 623. As noted above, an integrated system made in accord with the present invention can also include means for transferring collected particulates to a container. Tape 620' advances from a supply reel 624 onto a take-up reel 626. An electric motor coupled to take-up reel 626 rotates the take-up reel at a selected speed so that the tape passes under stream 621 of fluid 610. Particulates 614 impact on the coated impact collection surface of the tape and are carried toward the take-up reel by the moving tape.

Other elements of particle impact collector 621 include a fan 628, which is rotatably driven by an electric motor 630.

Fan 628 impels fluid 610 in stream 621 toward coated impact collection surface 623. Other types of fans or impellers can alternatively be used. For example, a centrifugal fan (not shown) can be employed to move the fluid. If the fluid in which the particulates are entrained is a liquid, a pump (not shown) would be used instead of fan 628 to move fluid 610 toward coated impact collection surface 623.

To obtain a concentrated sample of particulates 614 from those collected on coated impact collection surface 623a, particle impact collector 621 preferably includes a specimen container 636 that is filled with a collected sample through a funnel 634. A liquid 638 that is rich in the particulates collected on the coated impact collection surface partially fills sample container 636. Liquid 638 is obtained by washing the particulates from the tape. A reservoir 642 is included to supply the liquid for this purpose. The liquid from the reservoir is conveyed through a fluid line 644 and sprayed toward tape 610 through a nozzle 646, which creates a fan-shaped spray 648 that washes the particulates from the tape. If necessary, a pump, e.g., a centrifugal or a peristaltic pump (not shown) may be used to force the liquid through nozzle 646 under sufficient pressure to wash away the particulates retained by the coated impact collection surface. These particulates are carried by a stream 650 of the liquid into funnel 634 and thus are conveyed into sample container 636. Preferably, a relatively small volume of liquid is employed, so as to avoid unnecessarily diluting the sample.

The material used for producing coated impact collection surface 623 and other coated areas or surfaces employed in other embodiments discussed herein for collecting particulates in accord with the present invention is selected because of certain characteristics of the material that increase the efficiency with which the particulates are separated from the fluid in which they are entrained, and to enhance the removal of the particulates so that they may be transferred to a sample container. Each material used for a coating has certain advantages that may make it useful for separating a specific type of particulate from a specific type of fluid. For example, for use in particle impact collector 621, the TETRAGLYME™ material described above can be used for the coating. As noted above, this material is hydrophilic until it is exposed to water and when dry, is relatively tacky, tending to readily retain particulates that impact it, yet once water is sprayed onto the TETRAGLYME coated surface, such particulates readily released.

Figure 20A:
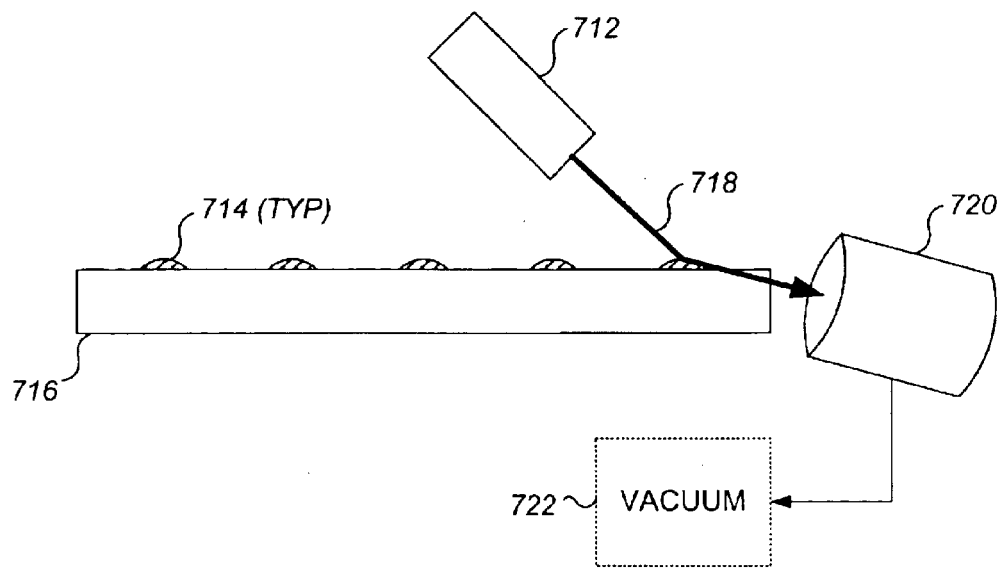
FIG. 20A is a block diagram of an embodiment in which a fluid jet is used to collect a sample of particles from a collection surface in accord with the present invention.
Figure 20B:
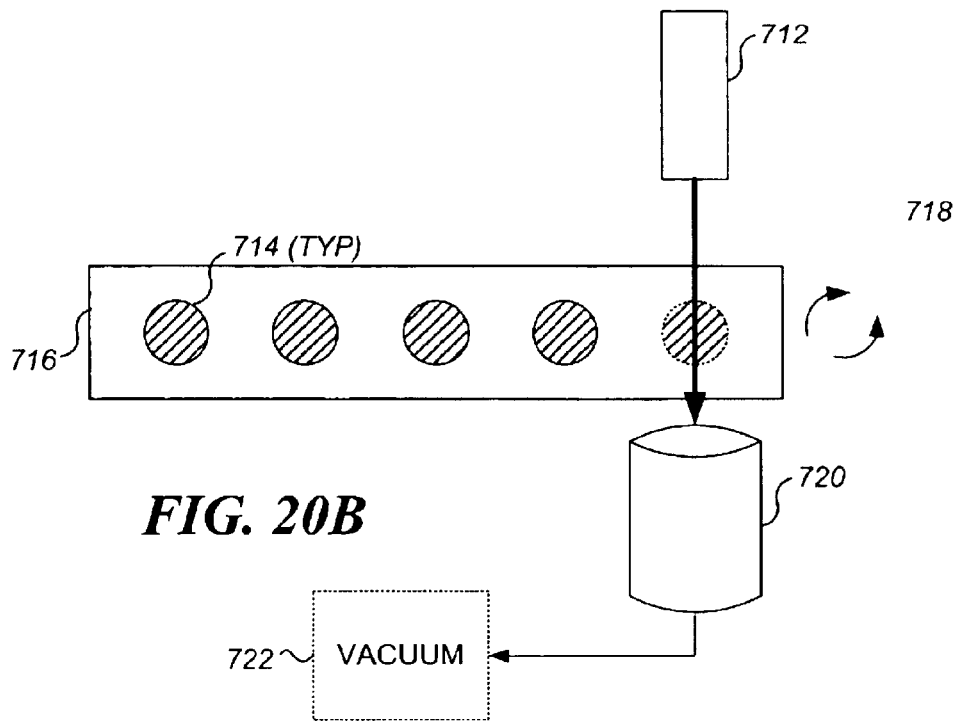
FIG. 20B is a block diagram of an embodiment in which the collection surface can be rotated 90 degrees to enable a fluid jet to be used to collect a sample of particles.

FIGS. 20A and 20B illustrate a fluid jet directed onto a collection surface, which may or may not be coated. The fluid may be a liquid (such as water) or a gas (such as air). Note that the difference between a liquid rinse and a gaseous jet is that the gaseous jet has significantly more kinetic energy than a liquid rinse. In a liquid rinse, the liquid is just acting as a carrier, picking particles up from the collection surface and rinsing them away. In contrast, use of a gaseous jet having substantially greater kinetic energy, there is a real mechanical action, where heat and friction created by the impinging high-velocity gas stream facilitate detachment of the particles from the surface. In a sense, the liquid rinse relies primarily on reduction of surface tension, and to a lesser extent, on the solvent power of the rinse liquid. The gaseous jet essentially blasts the particles off the collection surface and into a sample container.

FIG. 20A illustrates the use of a gaseous jet 718 to remove particles 714 from collection surface 716, and to transfer those particles into a sample container 720. Note that how the particles are deposited on the collection surface is not important in this Figure, since the Figure simply illustrates how such particles can be transferred to a sample container after they are collected. Source 712 of gaseous jet 718 may be directional, so that the gaseous jet is able to be directed at a particular deposit of particles on collection surface 716. It is also contemplated that source 712 can instead be fixed in position, and that instead, collection surface 716 can be moved relative to the fixed source to selectively impinge the gaseous jet on a particular group of particles.

FIG. 16 and the integrated system embodiment of the present invention that are discussed above provide details indicating how a collection surface can be moved. Note that it will generally be preferable that source 712 and the inlet used for directing particles toward the collection surface for collection not be disposed in substantially the same position. However, if both the inlet and source 712 are not operated simultaneously, such a configuration should not be a problem.

The fluid jet is directed at a selected group (or spot) of particles, which are "blasted" off the collection surface and into container 720. Container 720 should be properly positioned so that substantially all of the particles blasted from the collection surface are directed into the container. If desired, container 720 can be coupled in fluid communication with a vacuum source 722, so that particles are affirmatively drawn into container 720. Such a configuration reduces the likelihood of particles being dispersed in directions other than toward the sample container. Of course, a suitable filter must be employed to prevent the particles from escaping container 720 through the line that couples the vacuum source to the container. The angle at which fluid jet 718 is directed toward the collection surface should be selected to direct the blasted particles into the collection container.

When fluid jet 718 comprises a gas, the particles are transferred into the sample container without the use of any liquid, and no dilution of the sample has taken place. A further benefit of using a gas for the jet is that container 720 can be sealed and stored dry, so that a liquid is added only immediately before analysis of the sample stored in the sample container. This approach also reduces the weight of the sample, which can be important, particularly in an integrated system embodiment in which many samples are taken, since use of dry samples can significantly reduce the total weight of the samples. The gas selected for the fluid jet should be inert with respect to the particles collected, so that no undesired reactions occur between the sample particles and the gas. Preferred gases include compressed air, compressed nitrogen, compressed carbon dioxide, and inert gases such as argon.

When fluid jet 718 comprises a liquid, care should be taken not to use too much liquid, so that the sample of particles in not unduly diluted. Because of the energetic nature of the fluid jet, even a small amount of liquid is expected to be effective in transferring the particles from the collection surface and into the sample container.

FIG. 20B illustrates an embodiment in which the collection surface can be rotated by 90 degrees, so that source 712 can be disposed above particles 714, while container 720 is disposed below the particles. Fluid jet 718 is applied to cause the particles to fall directly into container 720. Once the particles are collected, the collection surface can be rotated by 90 degrees such that collection surface 716 is properly positioned to collect particles moving in the same direction as fluid jet 718. It should also be understood that the fluid stream into which the particles are originally entrained could be directed toward an impact collection surface that is not oriented horizontally, such that particles impact on an upper portion, but vertically, such that particles impact a side surface. In such an orientation, the collection surface would not need to be rotated by 90 degrees to enable the transfer of particles into a sample container as shown in FIG. 20B to be achieved. As noted above, container 720 can be placed in fluid communication with a vacuum 722.

Figure 21A:
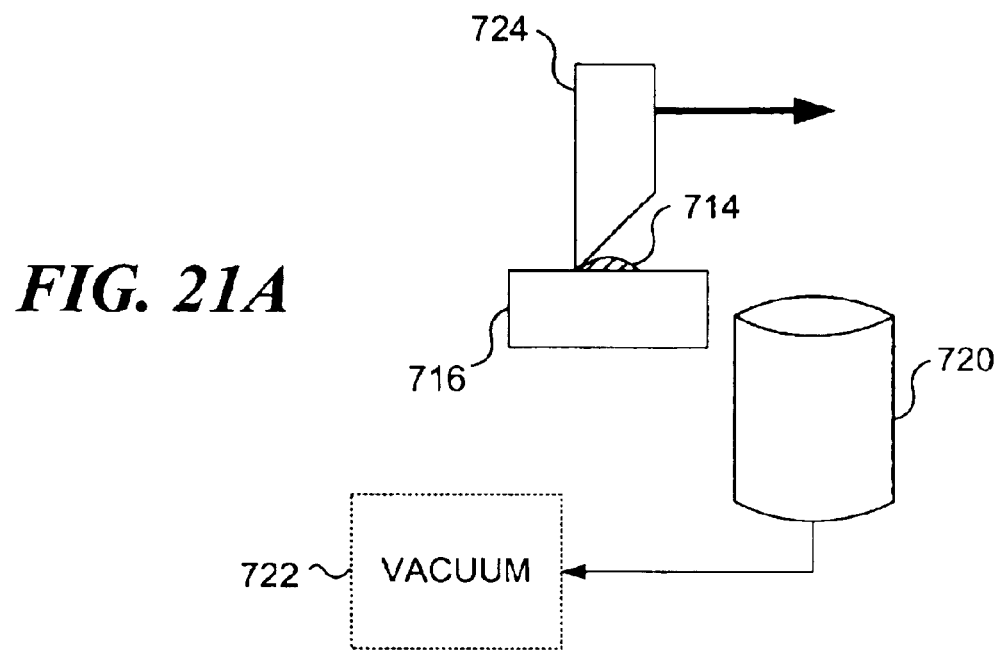
FIG. 21A is a side view of an embodiment in which a mechanical blade is used to collect a sample of particles from a collection surface in accord with the present invention.
Figure 21B:
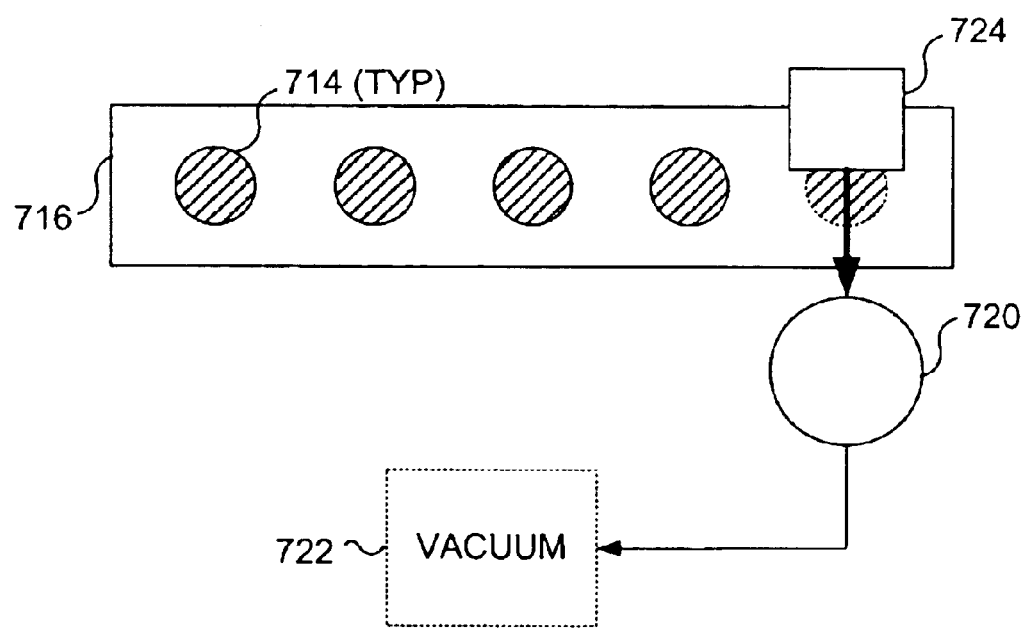
FIG. 21B is a plan view of an embodiment in which a mechanical blade is used to collect a sample of particles from a collection surface in accord with the present invention.
Figure 22:
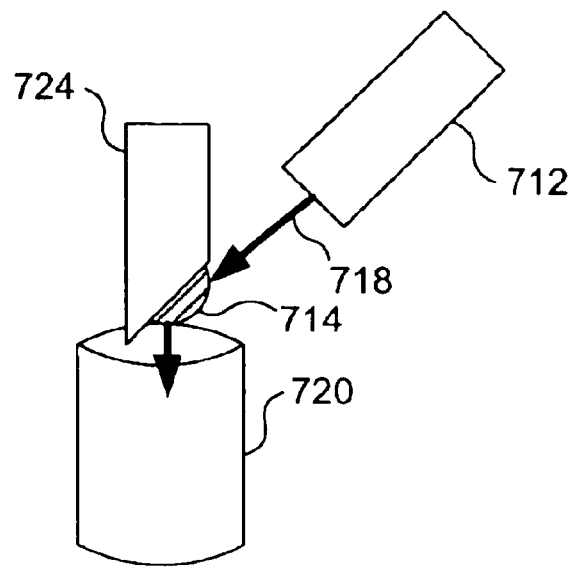
FIG. 22 is a block diagram illustrating an embodiment in which a mechanical blade is rinsed to remove particles from the blade.

A mechanical scraper 724 can be employed to remove and transfer selected particles 714 to container 720, as shown in the end view of FIG. 21A and plan view of FIG. 21B. A small volume of liquid can also be employed to rinse scraper 724, as shown in FIG. 22. As discussed above, the use of too much liquid should be avoided. Note that if scraper 724 is placed into container 720, then a gas jet can be employed to direct the particles into the container, enabling a dry sample to be collected. Particularly when container 720 is coupled in fluid communication with a vacuum, and a filter or trap is employed to prevent the particles from escaping the container, the use of a gas jet is not likely to result in dispersing the particles in undesired directions.

Another method of removing particles from scraper 724 without the use of a liquid rinse is to place the scraper in or immediately adjacent to container 720, and then to rapidly vibrate scraper 724, as is shown in FIG. 23. The vibrating action will tend to disperse any particles clinging to the scraper, and such particles will then fall into the container. As noted above, container 720 can be placed in fluid communication with a vacuum 722. Note that instead of, or in addition to vibrating scraper 724, the container itself can be vibrated. When container 720 contains a liquid, such vibrations will enhance the removal of particulates from the scraper.

Instead of removing the particles from the collection surface, in some embodiments, the portion of the collection surface containing a specific spot of particulates is removed and placed into a container. In a first such embodiment, shown in FIG. 24A, collection surface 716a is pre-scored into individual sections 728, enabling sections of the collection surface to be easily removed. Preferably the pre-scored sections are larger than the spot sizes, and smaller than the container. The pre-scored section is simply removed and placed in the container. No liquid is yet required, and the sample can be stored dry. Of course, the container can be filled with a desired quantity of liquid after, or even before, the portion of the surface is placed into the container. A punch 730 with a raised inner portion 732 enables the pre-scored portion to be removed without dislodging any of the particulates. In one embodiment, the punch will be disposed above the surface, and the container below the collection surface. Preferably, either the collection surface, or the container and punch can be repositioned to select a desired portion of the collection surface to remove.

If the collection surface is easily cut (such as a thin fiber or plastic material), then pre-scoring is not required. Particularly if the outer periphery of the punch is sharp, the punch will be able to remove unscored portions of such a thin collection surface. Note that the punch, or other member used to remove a portion of the collection surface, should not disturb the spot of particles on the collection surface.

Preferably the "punched" portion of the collection surface will fall into the container due to gravity. However, it may be useful for the container to be in fluid communication with a vacuum source as described above, to draw the removed portion into the container. A fluid jet 718 (preferably air) can be directed toward the cut portion of the collection surface to drive that portion into the container, however, such a jet has the potential to direct the particles in the spot in undesired directions (i.e. away from, rather than into, the container).

Note that a collection surface can be fabricated from a soluble material, such as starches or gelatin. When a portion of such a surface is placed into a container and a suitable liquid is added, the collection surface will dissolve, enabling the particles to freely disperse within the sample container. This can be quite beneficial, particularly in cases in which the presence of a portion of a collection surface in a liquid sample is not compatible with a particular analytical method.

It is anticipated that combinations of the above techniques can be useful. For example, a collection surface can be coated with a dissolvable coating, so that when a liquid jet is directed at that portion of the collection surface (see FIGS. 20A and 20B), the coating is dissolved and particles are readily removed. Another variation is to use a pre-scored collection surface coated with a dissolvable coating. After the pre-scored portion is placed in a container, and a liquid has been added to the container to dissolve the coating, the remaining portion of the collection surface can then be removed from the container.

Yet another variation, shown in FIG. 24B, is to employ a pre-scored collection surface 716b with a plurality of surface indentations 734. The particles are directed into the indentations, and then a normal punch 736 can be employed to remove the scored portions without disturbing the particles disposed in the indentation.

Preferable containers are plastic, although glass, metal, and ceramic can alternatively be employed. As with any sample container used to collect a sample for analysis, containers should be inert and clean, so that contaminants are not introduced into the sample.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive night is claimed is defined by the following:

1. Apparatus for separating and collecting particulates entrained in a flow of fluid, said apparatus comprising:
    (a) a virtual impactor capable of separating a fluid stream into a major flow and a minor flow, the major flow including a minor portion of particulates that are above a predetermined size and the minor flow including a major portion of the particulates that are above the predetermined size, said virtual impactor including a minor flow outlet through which the minor flow exits the virtual impactor;
    (b) at least one collection surface disposed adjacent to said virtual impactor, such that the minor flow of fluid moving through said minor flow outlet is directed toward said at least one collection surface, said at least one collection surface comprising a plurality of tickets, each ticket including a pair of deposition surfaces upon which particulates are to be deposited;
    (c) a prime mover drivingly coupled to one of said virtual impactor and at least one collection surface, causing a relative position of said virtual impactor and said at least one collection surface to be selectively changed over time, so that the minor flow of fluid moving through said minor flow outlet is directed, over time, towards one of a different portion of a specific one of said at least one collection surface, and a different one of said at least one collection surface; and (d) means for collecting a sample from said at least one collection surface, said means being configured to collect a sample from only one of said pair of deposition surfaces, particulates deposited on the other of said pair being saved for archival purposes, said means comprising at least one of:

(i) a member configured to remove a portion of said at least one collection surface, wherein particulates have been deposited on the portion; and (ii) a nozzle coupled to a supply of a gaseous fluid, the nozzle being configured to direct a jet of gaseous fluid towards said at least one collection surface, to dislodge particulates collected thereon.

2. Apparatus for separating and collecting particulates entrained in a flow of fluid, said apparatus comprising:

(a) a virtual impactor capable of separating a fluid stream into a major flow and a minor flow, the major flow including a minor portion of particulates that are above a predetermined size and the minor flow including a major portion of the particulates that are above the predetermined size, said virtual impactor including a minor flow outlet through which the minor flow exits the virtual impactor;

(b) at least one collection surface disposed adjacent to said virtual impactor, such that the minor flow of fluid moving through said minor flow outlet is directed toward said at least one collection surface, wherein said at least one collection surface can be rotated relative to said virtual impactor, to facilitate collection of a sample of particulates from said at least one collection surface;

(c) a prime mover drivingly coupled to one of said virtual impactor and at least one collection surface, causing a relative position of said virtual impactor and said at least one collection surface to be selectively changed over time, so that the minor flow of fluid moving through said minor flow outlet is directed, over time, towards one of a different portion of a specific one of said at least one collection surface, and a different one of said at least one collection surface; and (d) means for collecting a sample from said at least one collection surface, said means comprising at least one of:

(i) a member configured to remove a portion of said at least one collection surface, wherein particulates have been deposited on the portion; and (ii) a nozzle coupled to a supply of a gaseous fluid, the nozzle being configured to direct a jet of gaseous fluid towards said at least one collection surface, to dislodge particulates collected thereon.

3. Apparatus for separating and collecting particulates entrained in a flow of fluid, said apparatus comprising:

(a) a virtual impactor capable of separating a fluid stream into a major flow and a minor flow, the major flow including a minor portion of particulates that are above a predetermined size and the minor flow including a major portion of the particulates that are above the predetermined size, said virtual impactor including a minor flow outlet through which the minor flow exits the virtual impactor;

(b) at least one collection surface disposed adjacent to said virtual impactor, such that the minor flow of fluid moving through said minor flow outlet is directed toward said at least one collection surface;

(c) a prime mover drivingly coupled to one of said virtual impactor and at least one collection surface, causing a relative position of said virtual impactor and said at least one collection surface to be selectively changed over time, so that the minor flow of fluid moving through said minor flow outlet is directed, over time, towards one of a different portion of a specific one of said at least one collection surface, and a different one of said at least one collection surface;

(d) means for collecting a sample from said at least one collection surface, said means comprising at least one of:

(i) a member configured to remove a portion of said at least one collection surface, wherein particulates have been deposited on the portion; and (ii) a nozzle coupled to a supply of a gaseous fluid, the nozzle being configured to direct a jet of gaseous fluid towards said at least one collection surface, to dislodge particulates collected thereon; and (e) a trigger configured to be responsive to when a sample of particulates is to be collected, said means being then activated by the trigger to collect the sample from said at least one collection surface, wherein the trigger is responsive to a parameter other than a lapse of a predetermined period of time that indicates a sample has been deposited on said at least one collection surface.

4. The apparatus of claim 3, wherein said trigger comprises an optical cell configured to activate a sample collection by sensing that a level of particulates in the minor flow has reached a predefined threshold.

5. The apparatus of claim 3, wherein said trigger comprises a sensor configured to detect an environmental parameter indicative of a deposition of the sample on said at least one collection surface.

* * * * *